United States Patent [19]

Liverton et al.

[11] Patent Number: 5,859,041

[45] Date of Patent: Jan. 12, 1999

[54] SUBSTITUTED IMIDAZOLES HAVING CYTOKINE INHIBITORY ACTIVITY

[75] Inventors: Nigel J. Liverton, Harleysville; David A. Claremon, Maple Glen; John W. Butcher, Telford; Mark T. Bilodeau, Lansdale, all of Pa.

[73] Assignee: Merck & Co., Inc., Rahway, N.J.

[21] Appl. No.: 871,382

[22] Filed: Jun. 9, 1997

Related U.S. Application Data

[60] Provisional application No. 60/019,487, Jun. 10, 1996, and provisional application No. 60/023,312, Jul. 31, 1996.

[51] Int. Cl.$^6$ ...................... A61K 31/415; C07D 233/54; C07D 233/56; C07D 401/02
[52] U.S. Cl. .................... 514/396; 514/397; 514/825; 548/335.1; 548/342; 544/300
[58] Field of Search .................... 544/298, 300; 514/396, 397, 825; 548/335.1, 342

[56] References Cited

U.S. PATENT DOCUMENTS

| | | | |
|---|---|---|---|
| 3,707,475 | 12/1972 | Lombardino et al. | 260/309 |
| 3,772,441 | 11/1973 | Lombardino et al. | 424/273 |
| 3,929,807 | 12/1975 | Fitzi | 260/298.4 R |
| 3,940,486 | 2/1976 | Fitzi | 424/263 |

FOREIGN PATENT DOCUMENTS

| | | |
|---|---|---|
| WO 93/14081 | 7/1993 | WIPO . |
| WO 93/14082 | 7/1993 | WIPO . |
| WO 95/03297 | 7/1993 | WIPO . |
| WO 93/23381 | 11/1993 | WIPO . |
| WO 95/00501 | 1/1995 | WIPO . |
| WO 95/02591 | 1/1995 | WIPO . |
| WO 96/03387 | 2/1996 | WIPO . |

OTHER PUBLICATIONS

J. L. Adams, Chem. Abs. 126 (12, Abs No. 126:144274K, 1997).

*Primary Examiner*—C. H. Kelly
*Attorney, Agent, or Firm*—Elliott Korsen; Mark R. Daniel

[57] ABSTRACT

Compounds represented by formula I:

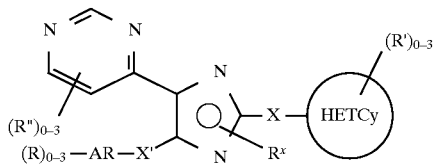

are disclosed. $A^R$ represents an aromatic group containing 6–10 atoms; and

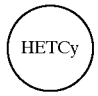

represents a 4 to 10 membered non-aromatic heterocycle containing at least one N atom, and optionally containing 1–2 additional N atoms and 0–1 O or S atom. A pharmaceutical composition is also included. Methods of treating cancer and cytokine mediated diseases are also included.

24 Claims, No Drawings

SUBSTITUTED IMIDAZOLES HAVING CYTOKINE INHIBITORY ACTIVITY

This is a provisional application Ser. No. 60/029,487 filed Apr. 10, 1996. This is a provisional application Ser. No. 60/023,312 filed Jul. 31, 1996.

BACKGROUND OF THE INVENTION

The present invention relates to substituted imidazole compounds which have cytokine inhibitory activity. Cytokine mediated diseases and cytokine inhibition, suppression and antagonism are used in the context of diseases or conditions in which excessive or unregulated production or activity of one or more cytokines occurs. Examples of cytokines which are effected typically include Interleukin-1 (IL-1), Interleukin-6 (IL-6), Interleukin-8 (IL-8) and Tumor Necrosis Factor (TNF).

Interleukin-1 (IL-1) and Tumor Necrosis Factor (TNF) are produced by a variety of cells which are involved in immunoregulation and other physiological conditions.

There are many disease states in which IL-1 is implicated. Examples are rheumatoid arthritis, osteoarthritis, endotoxemia, toxic shock syndrome, acute and chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes.

Interleukin-1 has been demonstrated to mediate a variety of biological activities thought to be important in immunoregulation and other physiological conditions. [See, e.g., Dinarello et al., Rev. Infect. Disease, 6, 51 (1984)]. The known biological activities of IL-1 include the activation of T helper cells, induction of fever, stimulation of prostaglandin or collagenase production, neutrophil chemotaxis, induction of acute phase proteins and the suppression of plasma iron levels.

Excessive or unregulated tumor necrosis factor (TNF) production or activity has been implicated in mediating or exacerbating rheumatoid arthritis, rheumatoid spondylitis, osteoarthritis, gouty arthritis, and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have also been shown to activate HIV replication in monocytes and/or macrophages [See Poli, et al., Proc. Natl. Acad. Sci., 87:782–784 (1990)], therefore, inhibition of monokine production or activity aids in limiting HIV progression. TNF has been implicated in various roles with other viral infections, such as the cytomegalovirus (CMV), influenza virus and the herpes virus.

Interleukin-6 (IL-6) is a cytokine effecting the immune system and hematopoiesis. It is produced by several mammalian cell types in response to agents such as IL-1, and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, endothelial cells and ketainocytes. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD11b/CD 18) on neutrophils without de novo protein synthesis.

There remains a need for compounds which are useful in treating cytokine mediated diseases, and as such, inhibit, suppress or antagonize the production or activity of cytokines such as IL-1, IL-6, IL-8 and TNF.

SUMMARY OF THE INVENTION

The present invention addresses a compound represented by formula I:

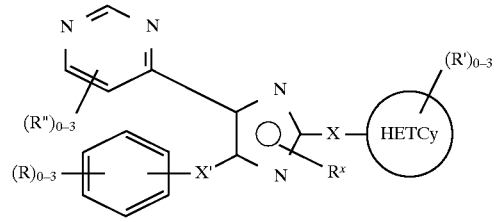

or a pharmaceutically acceptable salt thereof, wherein:

X and X' each independently represent —$(CH_2)_m$—Y—$(CH_2)_n$—, wherein m and n represent integers within the range of from 0–4, such that the sum of m and n is from 0–6; Y represents a member selected from the group consisting of: a direct bond; O; $S(O)_y$, with y equal to 0, 1 or 2; $NR^q$, with $R^q$ as defined below; C(O); OC(O); C(O)O; $SO_xNR^q$ with x equal to 1 or 2 and $R^{q'}$ as defined below; $NR^qSO_x$; $C(O)NR^q$ and $NR^qC(O)$;

represents a 4 to 10 membered non-aromatic heterocycle containing at least one N atom, and optionally containing 1–2 additional N atoms and 0–1 O or S atom;

$R^x$ represents H, $C_{1-6}$ alkyl($R^q)_3$, $C_{3-8}$ cycloalkyl, $OC_{1-6}$ alkyl($R^q)_3$ or $C(O)C_{1-6}$ alkyl($R^q)_3$;

each R independently represents a member selected from the group consisting of: halo; hydroxy; $C_{1-6}$ alkyl($R^q)_3$; $OC_{1-6}$ alkyl($R^q)_3$; $C_{3-8}$ cycloalkyl($R^q)_3$; CN; $CONH_2$; $CONHC_{1-6}$ alkyl($R^q)_3$; $CON(C_{1-6}$alkyl($R^q)_3)_2$; $NH_2$; $NHC_{1-6}$alkyl($R^q)_3$; $NHC_{3-8}$ cycloalkyl; $N(C_{1-6}$ alkyl$(R^q)_3)_2$; $CON(C_{3-8}$ cycloalkyl)($C_{1-6}$ alkyl($R^q)_3$)); $CO_2H$; $CO_2C_{1-6}$ alkyl($R^q)_3$; $C(O)C_{1-6}$ alkyl($R^q)_3$; aryl($R^q)_3$; heterocyclyl($R^q)_3$; heteroaryl($R^q)_3$; $CF_3$; SH; $NO_2$; $NHSO_2C_{1-6}$alkyl($R^q)_3$, $NHSO_2$aryl($R^q)_3$, $NHSO_2$heteroaryl($R^q)_3$; $N(R^{q'})C(O)C_{1-6}$ alkyl($R^q)_3$; $NR^{q'}C(O)NH(C_{1-6}$ alkyl($R^q)_3$); $C_{2-4}$ alkenyl($R^q)_{2-3}$ and $C_{2-4}$ alkynyl($R^q)_{1-3}$;

3 each R" independently represents a member selected from the group consisting of: halo; hydroxy; $C_{1-6}$alkyl($R^q$)$_3$; $OC_{1-6}$ alkyl($R^q$)$_3$; $C_{3-8}$ cycloalkyl($R^q$)$_3$; CN; $CONH_2$; $CONHC_{1-6}$ alkyl($R^q$)$_3$; $CON(C_{1-6}$ alkyl($R^q$)$_3$)$_2$; $NH_2$; $NHC_{1-6}$alkyl($R^q$)$_3$; $NHC_{3-8}$ cycloalkyl; $N(C_{1-6}$ alkyl $(R^q)_3)_2$; $CON(C_{3-8}$ cycloalkyl)($C_{1-6}$ alkyl($R^q$)$_3$)); $CO_2H$; $CO_2C_{1-6}$ alkyl($R^q$)$_3$; $C(O)C_{1-6}$alkyl($R^q$)$_3$; aryl ($R^q$)$_3$; heterocyclyl($R^q$)$_3$; heteroaryl($R^q$)$_3$; $CF_3$; SH; $NO_2$; $SO_yC_{1-6}$ alkyl($R^q$)$_3$, with y as defined above; $SO_2NH_2$; $SO_2NHC_{1-6}$ alkyl($R^q$)$_3$; $SO_2N(C_{1-6}$ alkyl($R^q$)$_3$)$_2$; $NHSO_2C_{1-6}$alkyl($R^q$)$_3$, $NHSO_2$aryl($R^q$)$_3$, $NHSO_2$heteroaryl($R^q$)$_3$; $N(R^{q'})C(O)C_{1-6}$ alkyl($R^q$)$_3$; $NR^{q'}C(O)NH(C_{1-6}$ alkyl($R^q$)$_3$); $C_{2-4}$ alkenyl($R^q$)$_{2-3}$ and $C_{2-4}$ alkynyl($R^q$)$_{1-3}$;

each R' independently represents a member selected from the group consisting of: $CONH_2$; $CONHC_{1-6}$ alkyl($R^q$)$_3$; $CON(C_{1-6}$ alkyl($R^q$)$_3$)$_2$; $CONHC_{3-8}$ cycloalkyl($R^q$)$_3$; $CON(C_{3-8}$ cycloalkyl($R^q$)$_3$)$_2$; $CON(C_{3-8}$ cycloalkyl)($C_{1-6}$ alkyl($R^q$)$_3$)); $CO_2H$; $CO_2C_{1-6}$ alkyl($R^q$)$_3$; $C(O)$ $C_{1-6}$ alkyl($R^q$)$_3$; $CO_2C_{3-8}$ cycloalkyl($R^q$)$_3$; $C(O)C_{3-8}$ cycloalkyl($R^q$)$_3$; —[$C(O)(CH_2)_j$—$CR^5R^6$—$(CH_2)_k$—$NR^7$]$_p$—$R^8$; —$C(O)C_{3-8}$ cycloalkyl($R^q$)$_3$; —$C(O)$ heterocyclyl($R^q$)$_3$; —$CON[C_{1-6}$ alkyl($R^q$)$_3$][$C_{3-8}$ cycloalkyl($R^q$)$_3$]; —$C(O)$aryl($R^q$)$_3$; —$C(O)$heteroaryl ($R^q$)$_3$; hydroxy; $C_{1-6}$ alkyl($R^q$)$_3$; $C_{3-8}$ cycloalkyl($R^q$)$_3$; $OC_{1-6}$ alkyl($R^q$)$_3$; $OC_{3-8}$ cycloalkyl($R^q$)$_3$; heterocyclyl ($R^q$)$_3$; CN; NH($R^{q'}$); $NHC_{1-6}$ alkyl($R^q$)$_3$; $N(C_{1-6}$ alkyl ($R^q$)$_3$)$_2$; $NHC_{3-8}$ cycloalkyl($R^q$)$_3$; $N(C_{3-8}$ cycloalkyl ($R^q$)$_3$)$_2$; $CF_3$; SH; $NO_2$; $C_{2-4}$ alkenyl($R^q$)$_{2-3}$, aryl($R^q$)$_3$; heteroaryl($R^q$)$_3$; $C_{2-4}$ alkynyl($R^q$)$_{1-3}$; —$OC(O)$ $C_{3-8}$ cycloalkyl($R^q$)$_3$; $SO_2NH_2$; $SO_2NHC_{1-6}$alkyl($R^q$)$_3$; $SO_2N(C_{1-6}$alkyl($R^q$)$_3$)$_2$; $NHSO_2$ $C_{1-6}$alkyl($R^q$)$_3$; $NHSO_2$aryl($R^q$)$_3$; $NHSO_2$heteroary($R^q$)$_3$; —$OC(O)$ heterocyclyl($R^q$)$_3$; $N(R^{q'})C(O)C_{1-6}$ alkyl($R^q$)$_3$; $NR^{q'}C(O)NH(C_{1-6}$ alkyl($R^q$)$_3$); —$OC(O)C_{1-6}$ alkyl($R^q$)$_3$; —$OC(O)$aryl($R^q$)$_3$; —$OC(O)$heteroaryl($R^q$)$_3$; —$C(=NR^{q'})NH_2$; —$C(=N^{q'})NHC_{1-6}$ alkyl($R^q$)$_3$; —$C(=N^{q'})N(C_{1-6}$ alkyl($R^q$)$_3$)$_2$;

$$-O\{C(O)-(CH_2)_j-CR^5R^6-(CH_2)_k-NR^7\}_pR^8 \text{ and}$$

$$\{NR^7(CH_2)_k-CR^5R^6-(CH_2)_j-C(O)\}_pOR^9$$

wherein j and k independently represent integers of from 0–3;

$R^5$ and $R^6$ are independently H, aryl, $C_{1-6}$ alkyl($R^q$)$_3$, or $CR^5R^6$ in combination represents a 3, 4, 5 or 6 membered cycloalkyl or heterocyclyl group, an aryl group or a heteroaryl group;

p represents 1, 2 or 3, with the proviso that when p represents 1, $CR^5R^6$ represents a 3, 4, 5 or 6 membered cycloalkyl group or a heterocyclyl group, an aryl group or a heteroaryl group, and at least one of j and k is 1, 2 or 3;

$R^7$ and $R^8$ are independently H, $C_{1-6}$ alkyl or aryl;

$R^9$ represents H, a negative charge balanced by a positively charged group or a protecting group;

$R^q$ represents a member selected from the group consisting of: $R^{q'}$; halo; CN; $CO_2H$; $CO_2C_{1-4}$ alkyl; $C(O)C_{1-4}$ alkyl ; NH($R^{q"}$); aryl($R^a$)$_3$; heteroaryl($R^a$)$_3$; $NHC_{1-4}$ alkyl; $N(C_{1-4}$ alkyl)$_2$; $CONH_2$; SH; $S(O)_yC_{1-6}$ alkyl($R^a$)$_3$; $C(O)NHC_{1-6}$ alkyl($R^a$)$_3$; $C(O)N(C_{1-6}$ alkyl($R^a$)$_3$)$_2$; $C_{3-8}$ cycloalkyl; $NHC(NH)NH_2$; -heteroalkyl($R^a$)$_3$; —$NHC(O)NH_2$;

4

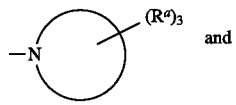

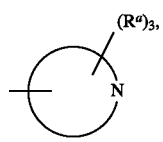

wherein

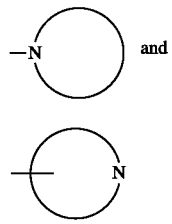

independently represent mono or bicyclic ring systems, non-aromatic or partially aromatic, containing from 5–10 ring atoms, 1–4 of which are N and 0–1 of which are O or $S(O)_y$, with y equal to 0, 1 or 2, optionally containing 1–2 carbonyl groups;

each $R^a$ independently represents a member selected from the group consisting of: H, $C_{1-6}$ alkyl, $OC_{1-6}$ alkyl, aralkyl, substituted aralkyl, heteroaralkyl, substituted heteroaralkyl, aralkoxy, substituted aralkoxy, halo, hydroxy, CN, $CONH_2$, $CONHC_{1-6}$ alkyl, $CON(C_{1-6}$ alkyl)$_2$, $CO_2H$, $CO_2C_{1-6}$ alkyl, $C(O)C_{1-6}$ alkyl, phenyl, $CF_3$, SH, $NO_2$, $SO_yC_{1-6}$ alkyl, with y as defined above; $SO_2NH_2$, $SO_2NHC_{1-6}$ alkyl, $NHSO_2$(substituted aryl), $NHSO_2$(substituted heteroaryl), $NHSO_2C_{1-6}$alkyl, $NHSO_2$aryl, $NHSO_2$heteroaryl, $NH_2$, $NHC_{1-6}$ alkyl, $N(C_{1-6}$ alkyl)$_2$, $NHC(O)C_{1-6}$ alkyl, $NHC(O)NH(C_{1-6}$ alkyl), $C_{2-4}$ alkenyl and $C_{2-4}$ alkynyl;

$R^{q'}$ represents H, OH, $C_{1-4}$ alkyl, —$OC_{1-4}$ alkyl, aryl or $C(O)C_{1-4}$ alkyl, and $R^{q"}$ represents H, OH or $OC_{1-4}$ alkyl.

A pharmaceutical composition is also included in the invention described herein, which is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective for treating said cytokine mediated disease.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight or branched, and when of sufficient size, e.g., $C_{3-15}$ may be cyclic. Preferred straight or branched alkyl groups include methyl, ethyl, propyl, isopropyl, butyl and t-butyl. Preferred cycloalkyl groups include cyclopropyl, cyclopentyl and cyclohexyl.

Alkyl also includes an alkyl group substituted with a cycloalkyl group, such as cyclopropylmethyl.

Alkyl also includes a straight or branched alkyl group which contains or is interrupted by a cycloalkylene portion. Examples include the following:

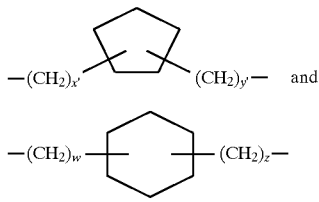

wherein:

x' and y'=from 0–10; and w and z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

Heteroalkyl means an alkyl group containing from 2–15 carbon atoms and being interrupted by from 1–4 heteroatoms selected from O, S and N.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydroimidazo[4,5-c] pyridine, phthalidyl and saccharinyl, as defined below.

Each $R^a$ independently represents a member selected from the group consisting of: H, $C_{1-6}$ alkyl, $OC_{1-6}$ alkyl, aralkyl, substituted aralkyl, heteroaralkyl, substituted heteroaralkyl, aralkoxy, substituted aralkoxy, halo, hydroxy, CN, $CONH_2$, $CONHC_{1-6}$ alkyl, $CON(C_{1-6}$ alkyl$)_2$, $CO_2H$, $CO_2C_{1-6}$ alkyl, $C(O)C_{1-6}$ alkyl, phenyl, $CF_3$, SH, $NO_2$, $SO_yC_{1-6}$ alkyl, with y as defined above; $SO_2NH_2$, $SO_2NHC_{1-6}$ alkyl, $NHSO_2$(substituted aryl), $NHSO_2$ (substituted heteroaryl), $NHSO_2C_{1-6}$alkyl, $NHSO_2$aryl, $NHSO_2$heteroaryl, $NH_2$, $NHC_{1-6}$ alkyl, $N(C_{1-6}$ alkyl$)_2$, $NHC(O)C_{1-6}$ alkyl, $NHC(O)NH(C_{1-6}$ alkyl), $C_{2-4}$ alkenyl and $C_{2-4}$ alkynyl. In substituted aralkyl, substituted heteroaralkyl and substituted aralkoxy, the aryl, heteroaryl or alkyl portions thereof can be substituted as appropriate.

Substituted alkyl, aryl and heteroaryl, and the substituted portions of aralkyl, aralkoxy, heteroaralkyl, heteroaralkoxy and like groups are substituted with from 1–3 groups selected from the group consisting of: halo, hydroxy, cyano, acyl, acylamino, aralkoxy, alkylsulfonyl, arylsulfonyl, alkylsulfonylamino, arylsulfonylamino, alkylaminocarbonyl, alkyl, alkoxy, aryl, aryloxy, aralkoxy, amino, alkylamino, dialkylamino, and sulfonylamino.

The terms "heterocycloalkyl" and "heterocyclyl" refer to a cycloalkyl group (nonaromatic) in which one of the carbon atoms in the ring is replaced by a heteroatom selected from O, $S(O)_y$ or N, and in which up to three additional carbon atoms may be replaced by said heteroatoms. When three heteroatoms are present in the heterocycle, they are not all linked together.

Examples of heterocyclyls are piperidinyl, morpholinyl, azetidinyl, pyrrolidinyl, tetrahydrofuranyl, imidazolinyl, piperazinyl, pyrolidin-2-one, piperidin-2-one and the like.

Acyl as used herein refers to —$C(O)C_{1-6}$ alkyl and —C(O)-aryl.

Acylamino refers to the group —$NHC(O)C_{1-6}$ alkyl and —NHC(O)aryl.

Aralkoxy refers to the group —$OC_{1-6}$ alkylaryl.

Alkylsulfonyl refers to the group —$SO_2C_{1-6}$ alkyl.

Alkylsulfonylamino refers to the group —$NHSO_2C_{1-6}$alkyl.

Arylsulfonylamino refers to the group —$NHSO_2$aryl.

Alkylaminocarbonyl refers to the group —$C(O)NHC_{1-6}$ alkyl.

Aryloxy refers to the group —O-aryl.

Sulfonylamino refers to the group —$NHSO_3H$.

Halo means Cl, F, Br and I selected on an independent basis.

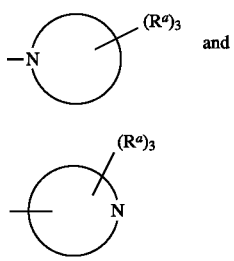

are optional substituents linked to the HETCy group.

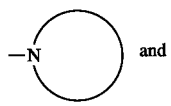 and

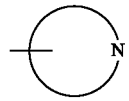

independently represent mono or bicyclic ring systems, non-aromatic or partially aromatic, containing from 5–10 ring atoms, 1–4 of which are N and 0–1 of which are O or S(O)$_y$, with y equal to 0, 1 or 2, and when partially aromatic, the non-aromatic portion thereof optionally containing 1–2 carbonyl groups. Hence, these ring systems can be heteroaryl or heterocyclic as defined above.

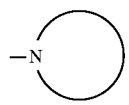

is linked to HETCy through a nitrogen atom contained in the ring system, either directly or through a linking group which is part of R'. Examples include phthalidyl and saccharinyl, as further defined below.

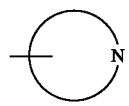

is likewise linked to HETCy, but through a carbon atom contained in the ring system.

The term phthalidyl refers to the heteroaryl group:

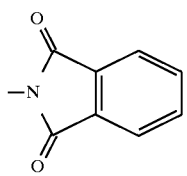

The term saccharinyl refers to the heteroaryl group:

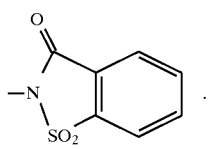

The group

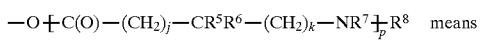
means

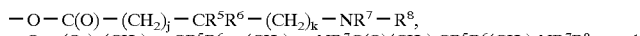
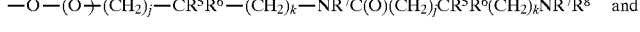

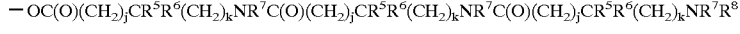

Likewise, the group

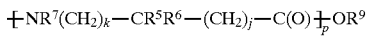

means $$-NR^7-(CH_2)_k-CR^5R^6-(CH_2)_j-C(O)-OR^9,$$

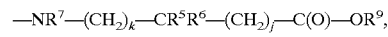

or

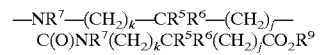

The variables are determined independently within each group. Thus, e.g., when more than one j is present, they may be the same or different. The values of $R^5$ and $R^6$ can be H, $C_{1-6}$ alkyl$(R^q)_3$ or aryl, or $CR^5R^6$ taken in combination represents a 3–6 membered cycloalkyl or heterocyclyl group, an aryl group or a heteroaryl group. Examples of suitable $CR^5R^6$ groups include:

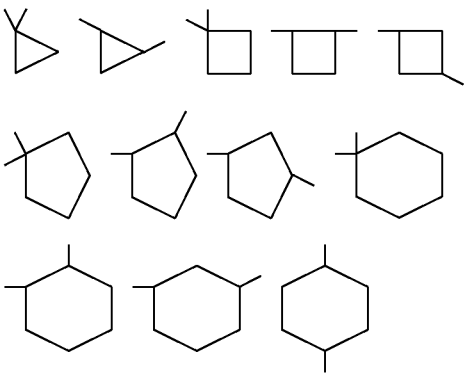

The patterns of attachment noted above can also include heteroatoms as appropriate. When an aryl or heteroaryl group is represented by $CR^5R^6$, attachment cannot be through the same carbon atom.

The term "TNF mediated disease or disease state" refers to disease states in which TNF plays a role, either by production or increased activity levels of TNF itself, or by causing another monokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1

(IL-1), Interleukin-6 (IL-6), Interleukin-8 (IL-8), Tumor Necrosis Factor-alpha (TNF-a) and Tumor Necrosis Factor-beta (TNF-b).

By the term "cytokine interfering or cytokine suppresive amount" is mean an effective amount of a compound of formula I which will cause a decrease in the in vivo activity or level of the cytokine to normal or sub-normal levels, when given to the patient for the prophylaxis or therapeutic treatment of a disease state which is exacerbated by, or caused by, excessive or unregulated cytokine production or activity.

The compounds of the present invention may contain one or more asymmetric carbon atoms and may exist in racemic and optically active forms. All are within the scope of the present invention.

One subset of compounds of particular interest is described with respect to formula I wherein one or two R" groups are present, and each independently represents $NH_2$, $NHC_{1-6}$ alkyl$(R^q)_3$, $N(C_{1-6}$ alkyl$)_2$, $NHC_{3-8}$ cycloalkyl, $N(R^q)C(O)C_{1-6}$ alkyl$(R^q)_3$, $C_{1-6}$ alkyl$(R^q)_3$, $OC_{1-6}$ alkyl$(R^q)_3$, $CO_2H$, $CONH_2$, $NR^qC(O)NHC_{1-6}$ alkyl$(R^q)^3$ or heterocyclyl$(R^q)_3$. Within this subset of compounds, all other variables are as previously defined.

Another subset of interest includes compounds of formula I wherein HETCy represents a 5–6 membered non-aromatic heterocycle with 1–2 nitrogen atoms contained therein. HETCy is preferably a pyrrolidinyl or piperidinyl group, and most preferably a 4-piperidinyl group. Within this subset of compounds, all other variables are as previously defined.

Another subset of compounds is represented by formula I wherein R' is selected from $C_{1-6}$ alkyl$(R^q)_3$, $OC_{1-6}$ alkyl$(R^q)_3$, —$C(O)C_{1-6}$ alkyl$(R^q)_3$; CN, $NO_2$ and $CO_2C_{1-6}$ alkyl$(R^q)_3$. Within this subset of compounds, all other variables are as previously defined.

Another subset of interest includes compounds of formula I wherein from 1–3 R groups are present and each independently represents a member selected from the group consisting of: halo, hydroxy, $C_{1-6}$ alkyl$(R^q)_3$, $OC_{1-6}$ alkyl$(R^q)_3$, $NH_2$, $NHC_{1-6}$ alkyl$(R^q)_3$, $N(C_{1-6}$ alkyl$(R^q)_3)_2$ and $CF_3$. Within this subset of compounds, all other variables are as previously defined.

More particularly, a subset of interest relates to compounds of formula I wherein one or two R groups are present, selected from halo and $CF_3$. Within this subset of compounds, all other variables are as previously defined.

Another subset of compounds is represented by formula I wherein $R^x$ is H, $C_{3-8}$ cycloalkyl or $C_{1-6}$ alkyl$(R^q)_3$. More particularly, $R^x$ represents H, $CH_3$, $CH_2CH_3$, $CH_2CH_2CH_3$, $CH_2CH_2CH_2CH_3$,

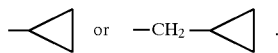

Within this subset of compounds, all other variables are as previously defined.

Another subset of compounds is represented by formula I wherein X' represents a direct bond. Within this subset of compounds, all other variables are as previously defined.

Another subset of compounds is represented by formula I wherein X represents —$(CH_2)_m$—Y—$(CH_2)_n$—, Y represents a direct bond, O, S or C(O); m represents 0 or 1 and n represents 0 or 1. Within this subset, X preferably represents a direct bond. Within this subset of compounds, all other variables are as previously defined.

A preferred subset of compounds is represented by formula I wherein:
one or two R" groups are present, each independently representing $NH_2$, $NHC_{1-6}$ alkyl$(R^q)_3$, $N(C_{1-6}$ alkyl$)_2$, $NHC_{3-8}$ cycloalkyl, $N(R^q)C(O)C_{1-6}$ alkyl$(R^q)_3$, $C_{1-6}$ alkyl$(R^q)_3$, $OC_{1-6}$ alkyl$(R^q)_3$, $CO_2H$, $CONH_2$, $NR^qC(O)NHC_{1-6}$ alkyl$(R^q)^3$ or heterocyclyl$(R^q)_3$;

HETCy represents a 5–6 membered non-aromatic heterocyclyl with 1–2 nitrogen atoms contained therein;

R' is selected from $C_{1-6}$ alkyl$(R^q)_3$, $OC_{1-6}$ alkyl$(R^q)_3$, —$C(O)C_{1-6}$ alkyl$(R^q)_3$; CN; $NO_2$; and $CO_2C_{1-6}$ alkyl$(R^q)_3$;

from 1–3 R groups are present and each independently represents a member selected from the group consisting of: halo, hydroxy, $C_{1-6}$ alkyl$(R^q)_3$, $OC_{1-6}$ alkyl$(R^q)_3$, $NH_2$, $NHC_{1-6}$ alkyl$(R^q)_3$, $N(C_{1-6}$ alkyl$(R^q)_3)_2$ $CO_2H$ and $CF_3$;

$R^x$ is H, $C_{3-8}$ cycloalkyl or $C_{1-6}$ alkyl$(R^q)_3$;

X' represents a direct bond;

X represents —$(CH_2)_m$—Y—$(CH_2)_n$—, Y represents a direct bond; m represents 0 or 1 and n represents 0 or 1.

A more preferred subset of compounds of the invention is represented by formula I wherein:
one or two R" groups are present, selected from the group consisting of: $NH_2$, $NHC_{1-6}$ alkyl$(R^q)_3$, $N(C_{1-6}$ alkyl$)_2$, $C_{1-6}$ alkyl$(R^q)_3$, $OC_{1-6}$ alkyl$(R^q)_3$ and heterocyclyl$(R^q)_3$;

HETCy represents a piperidinyl group;

zero or one R' is present, which is selected from $C_{1-6}$ alkyl$(R^q)_3$, —$CO_2C_{1-6}$ alkyl$(R^q)_3$ and —$C(O)C_{1-6}$ alkyl$(R^q)_3$;

one or two R groups are present, selected from halo and $CF_3$;

$R^x$ is H, $C_{3-8}$ cycloalkyl or $C_{1-6}$ alkyl$(R^q)_3$; and

X and X' represent a direct bond.

A more preferred subset of compounds of the invention is represented by formula I wherein:
one R" group is present and is selected from:

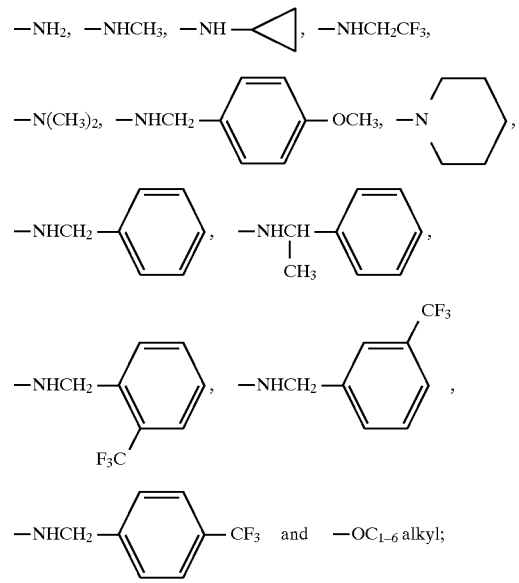

HETCy represents a 4-piperidinyl group;

R' is absent;

one or two R groups are present selected from halo and $CF_3$;

$R^x$ represents H, CH$_3$
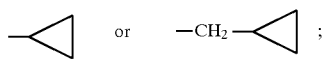
and X and X' represent direct bonds.
Representative species falling within the present invention include the following:
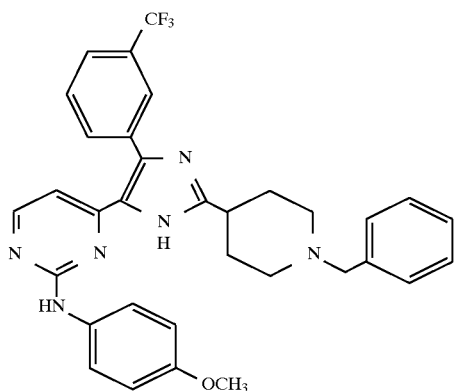
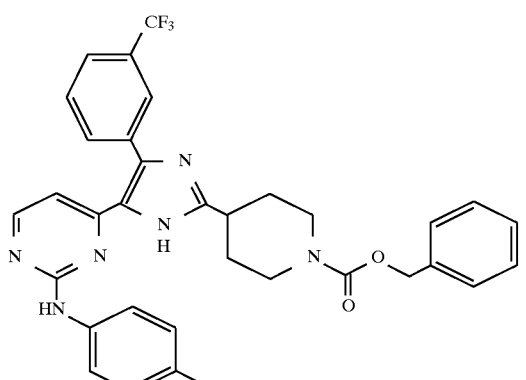
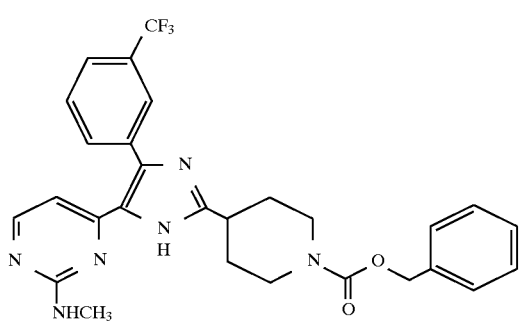
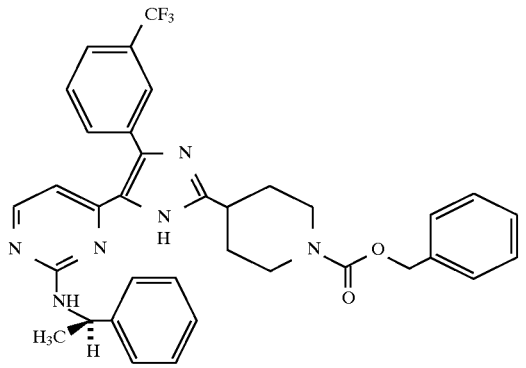
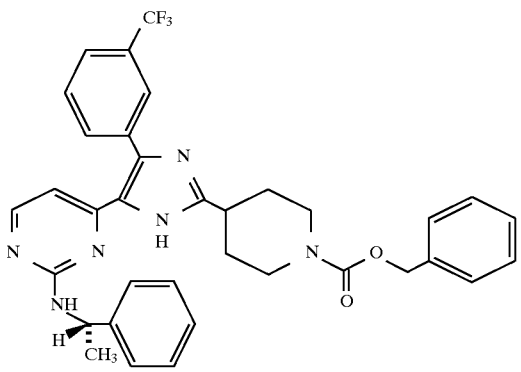
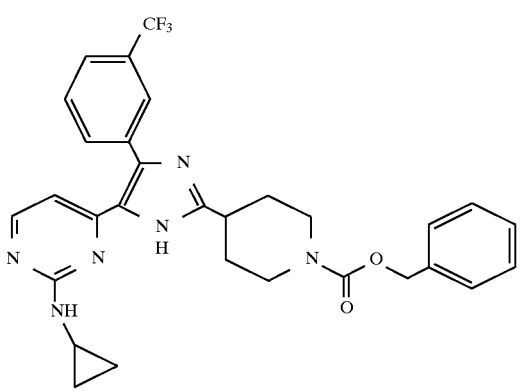
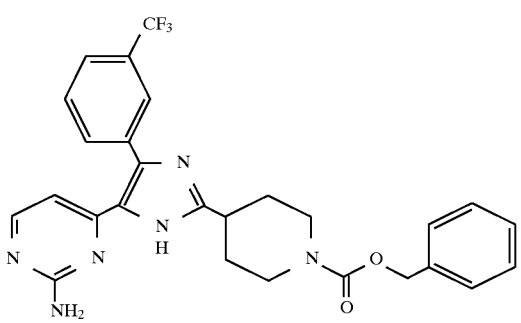
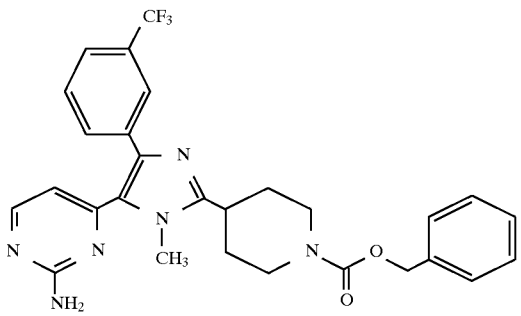

-continued
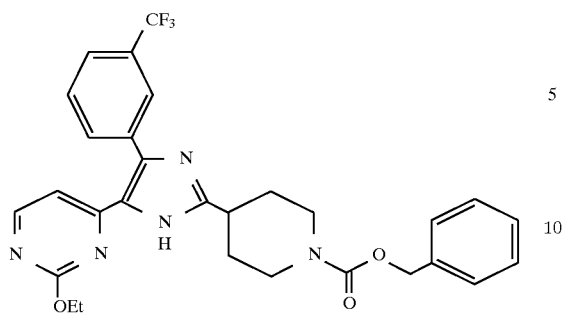
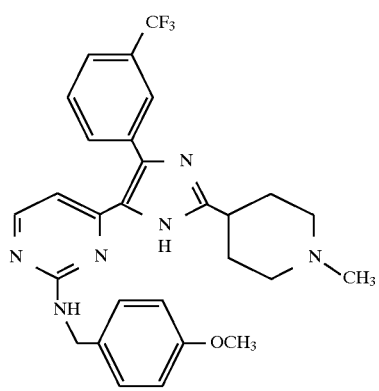
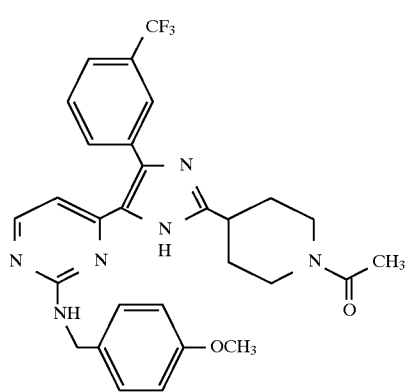
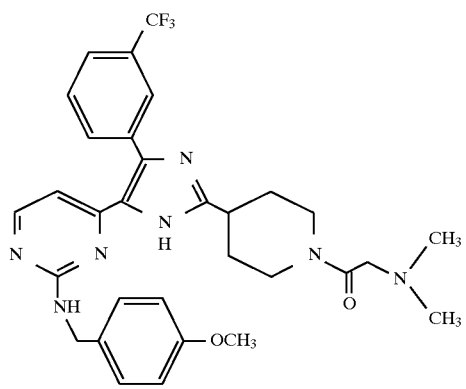
-continued
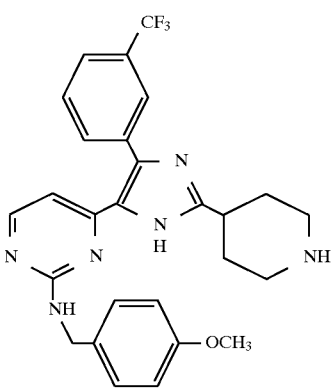
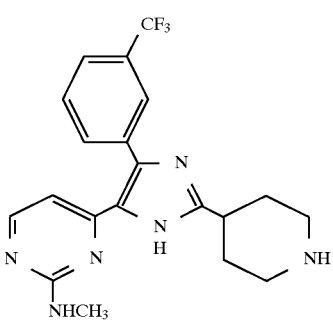
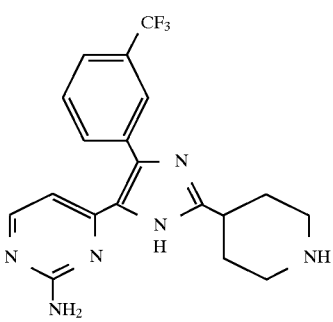
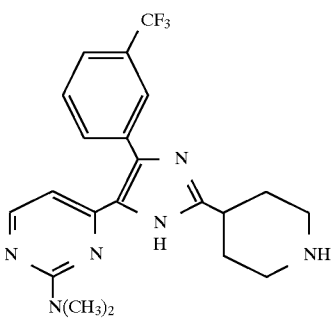

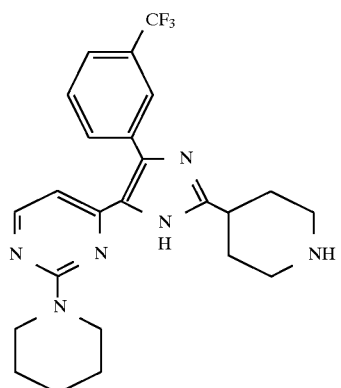
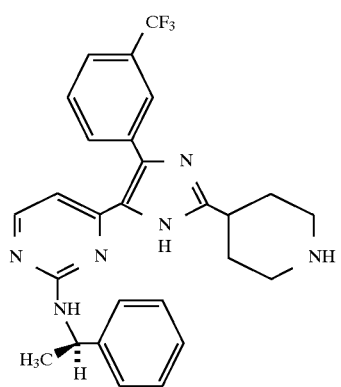
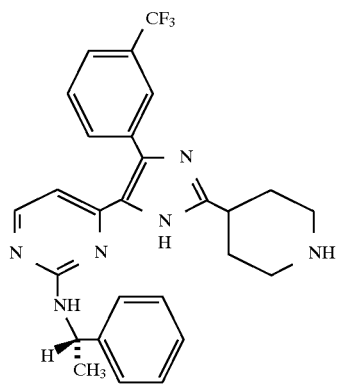
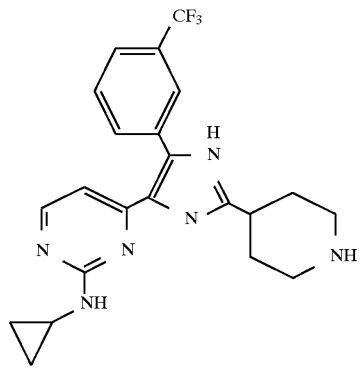
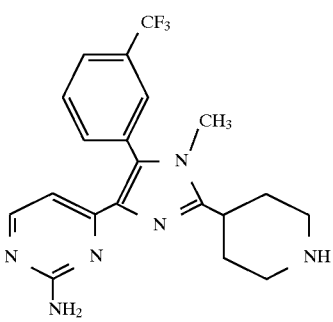
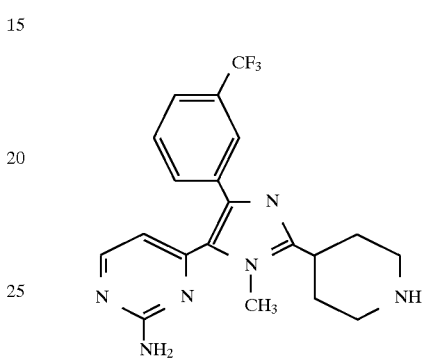
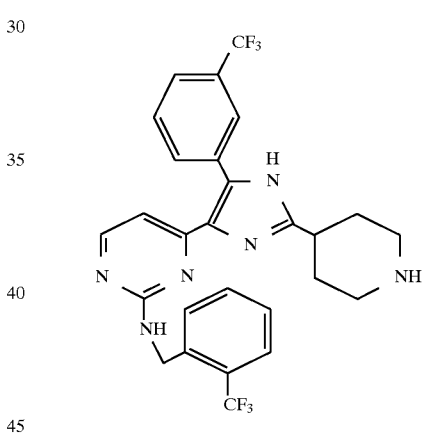
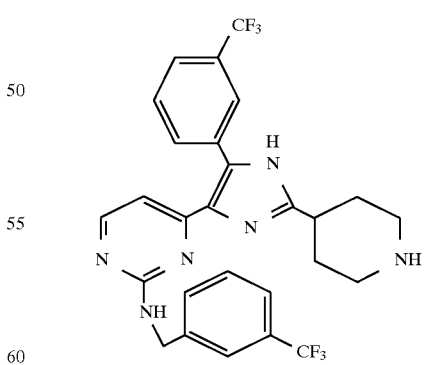

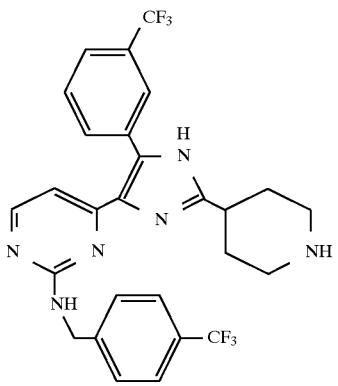
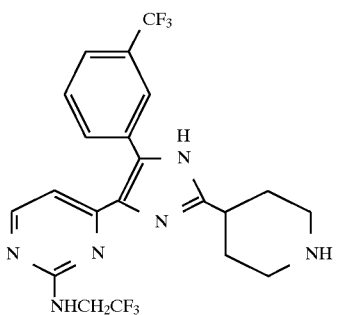
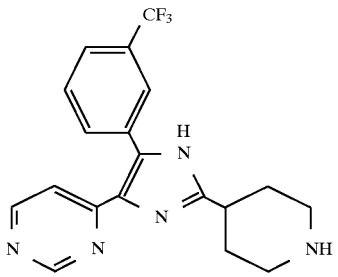
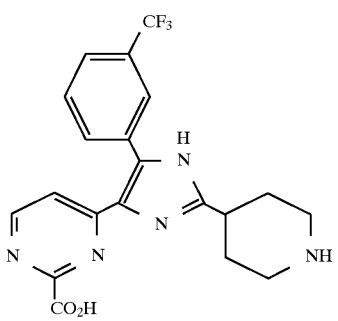
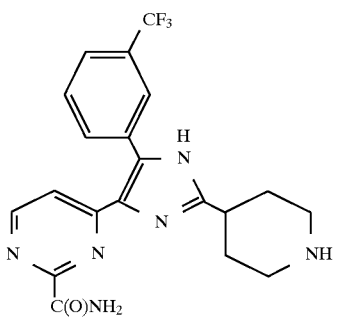
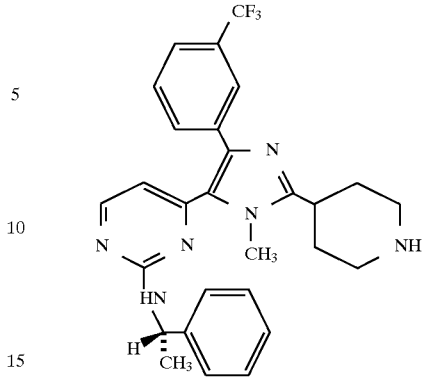

As used herein, THF means tetrahydrofuran, DMF means dimethylformamide and HOBT means hydroxybenzotriazole.

The compounds of the present invention are prepared by procedures illustrated in the accompanying schemes. The general method of preparing the imidazole nucleus is outlined in Scheme 1. 2-Mercaptopyrimidine 1 (commercially available from Aldrich Chemicals Inc) is reacted with a dialkyl dimethylformamide acetal such as dimethyl formamide dimethyl acetal in solvent (e.g. toluene) in the presence of a base e.g. diisopropylethylamine. Deprotonation of the product 2 with a strong base such as lithium diisopropylamide and quenching of the anion with an appropriately substituted N,O-dimethylhydroxamide 3 provides a ketone 4. Formation of the oximoketone 5 may be carried out under acidic conditions with either an inorganic nitrite (e.g. sodium nitrite) or an organic nitrite (e.g. t-butyl nitrite). Reaction of the oximinoketone with a suitably functionalized and protected amino aldehyde and an ammonium salt (e.g. ammonium acetate) in acetic acid leads to a hydroxyimidazole 6. Reduction to the imidazole 7 may be accomplished by a number of methods described in the literature (hydrogenation, reaction with $PCl_3$ or titanium trichloride). The imidazole may then be alkylated either by reaction with an alkyl halide and base in solvent (e.g. methyl iodide, cesium carbonate, DMF) or by heating with a dimethylformamide dialkyl acetal neat or in a solvent (e.g. dimethylformamide dimethyl acetal in toluene) to provide a mixture of isomers 8 and 9, separable by chromatography.

As shown in Scheme 2, the methylthiopyrimidine can be oxidized to the methylsulfonylpyrimidine, for example with oxone in methanol and then the methylsulfonyl group displaced with an amine to provide an aminopyrimidine derivative. Deprotection of the benzyloxycarbonyl protecting group could then be accomplished by treatment with hydrogen bromide in acetic acid or aqueous hydrochloric acid.

Scheme 3 illustrates compounds that may be obtained after the amine displacement reaction described in Scheme 2, where the amine utilized was 4-methoxybenzylamine. Reduction of the intermediate 10 with lithium aluminum hydride affords the N-methypiperidine derivative 13, Treatment with hydrogen bromide in acetic acid provides the piperidine 12 and treatment with hydrochloric acid at reflux leads to 11. The piperidine of compound 12 can be further reacted for example by reductive alkylation to provide 14 or by acylation to provide compounds 15.

Alternatively the methanesulfonyl group can be displaced with cyanide as shown in Scheme 4 to afford 17. Compound 17 may then be converted to a number of different products. Utilizing refluxing hydrochloric acid leads to the parent pyrimidine 19, whereas hydrogen bromide in acetic acid gives the carboxamide 20, which can be hydrolyzed to the acid 21 under basic conditions, e.g. aqueous sodium hydroxide solution.

Reactions on the piperidine nitrogen may also be carried out prior to the displacement of the sulfonylpyrimidine as shown in Scheme 5. The piperidine nitrogen of 22 may be acylated, for example employing EDC, HOBt and triethylamine and an appropriate carboxylic acid in DMF to give 23 and then the sulfonyl group displaced with an amine, e.g. ammonia to provide 24.

The aminopyrimidine can also be acylated, for example by treatment with an appropriate acid chloride (Scheme 6) to give 26 from which the protecting group can be removed with hydrogen bromide in acetic acid, yielding compounds 27.

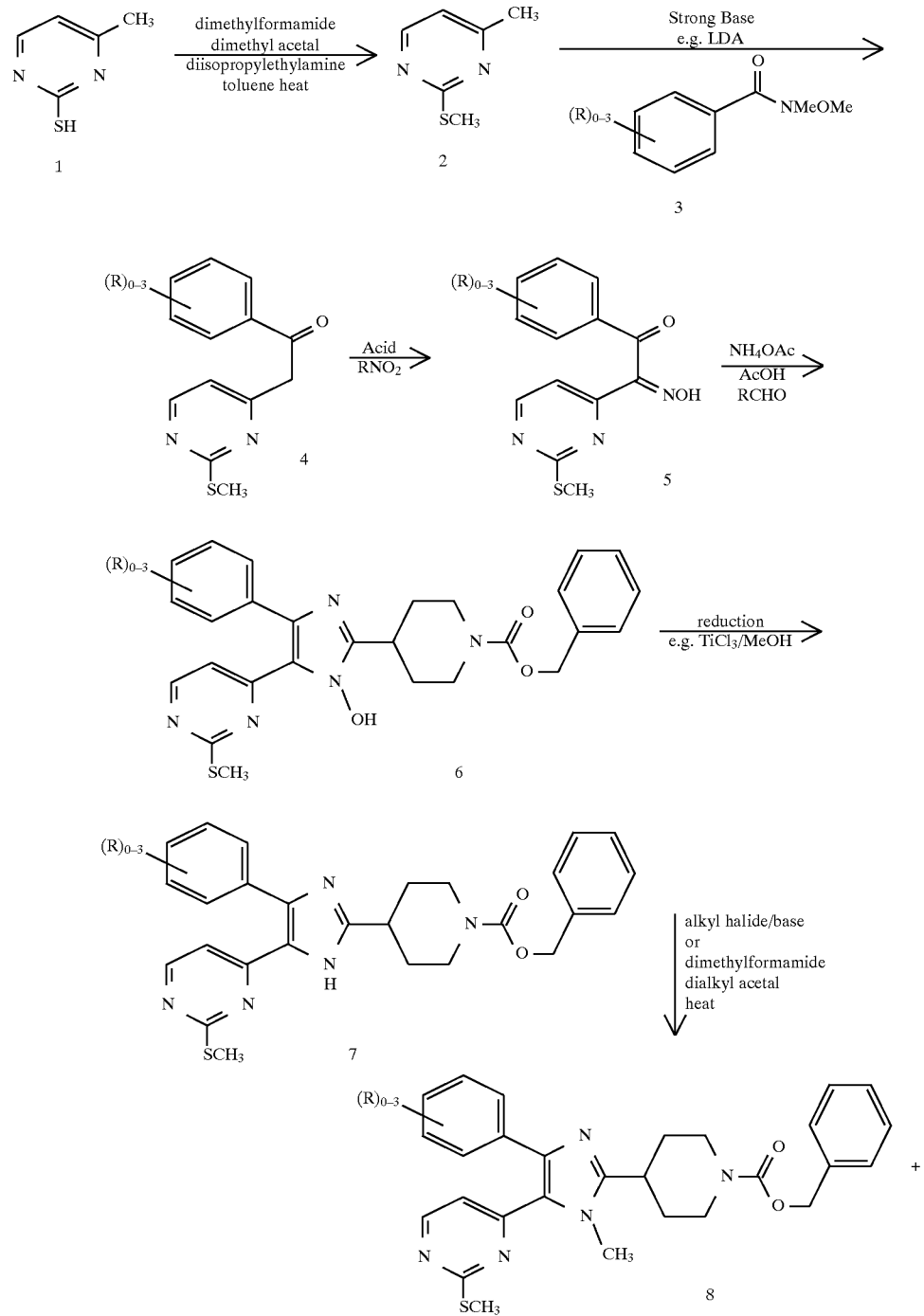

SCHEME 1

-continued
SCHEME 1
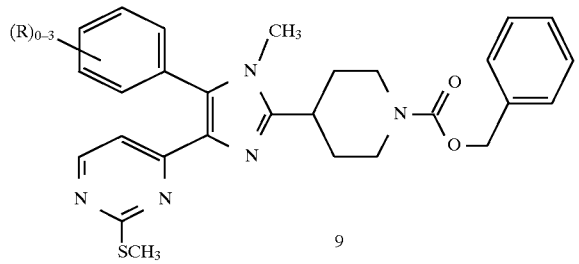
SCHEME 2
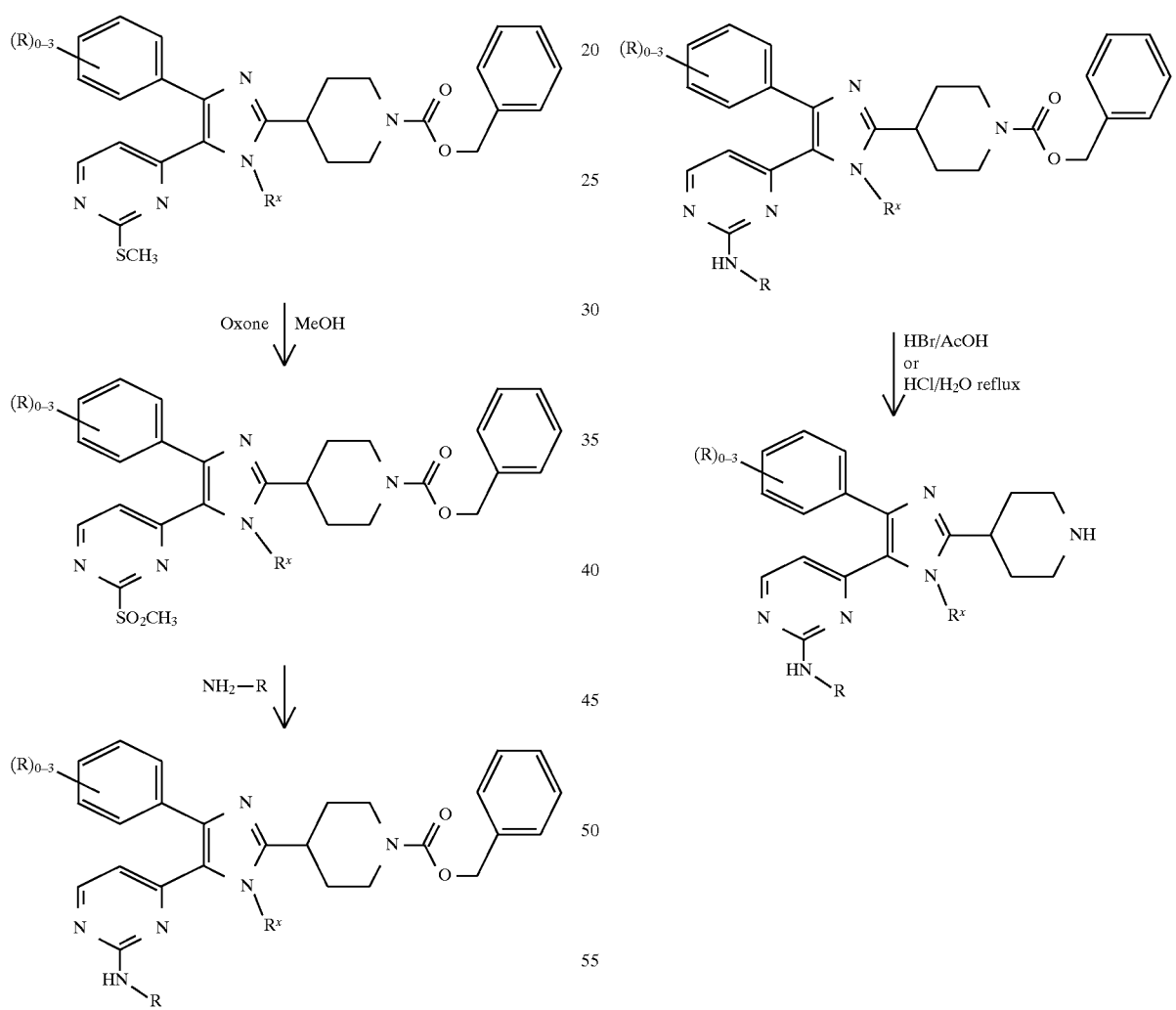

SCHEME 3
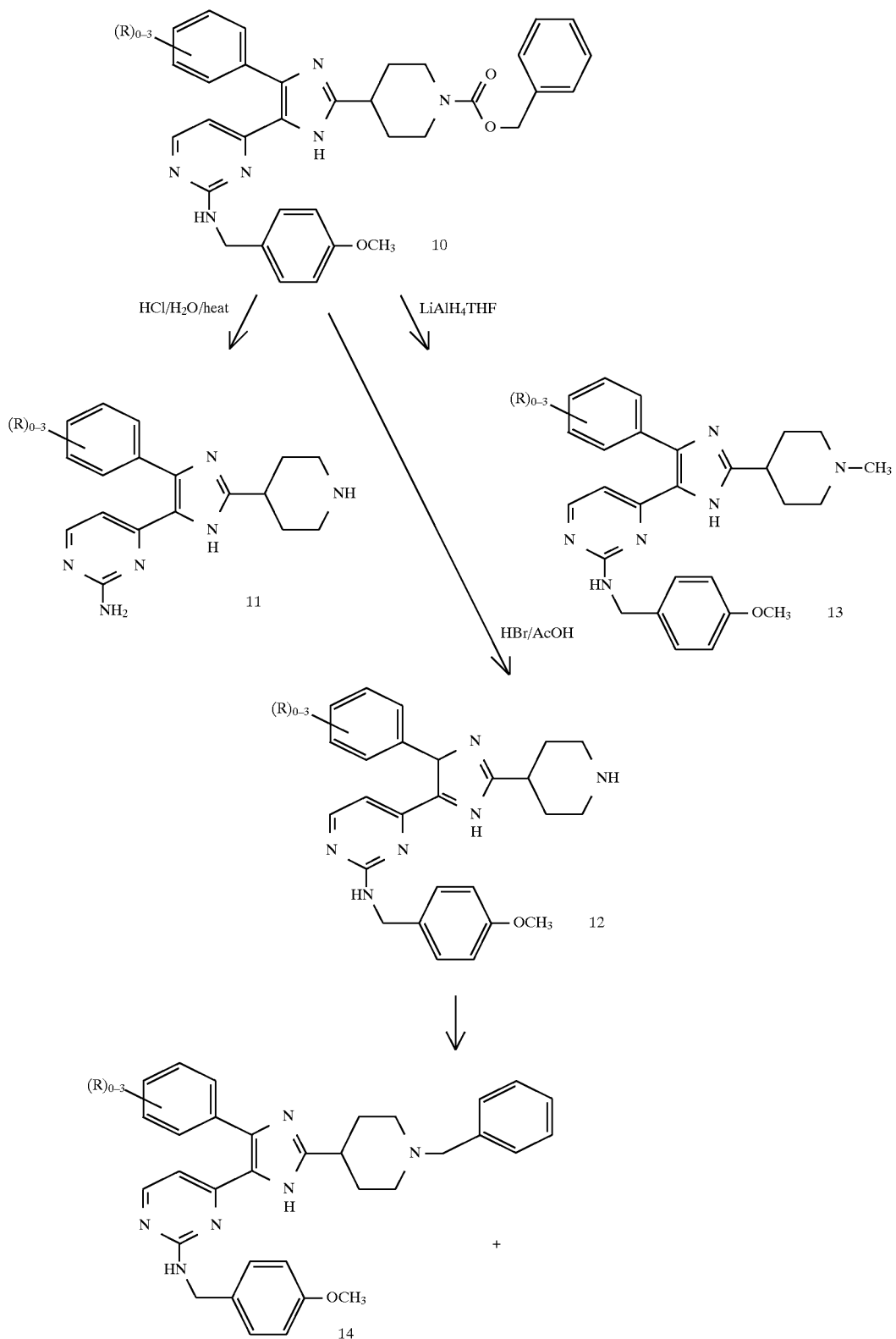

-continued
SCHEME 3
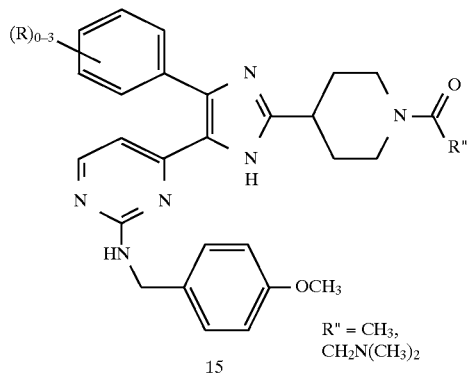
Scheme 4
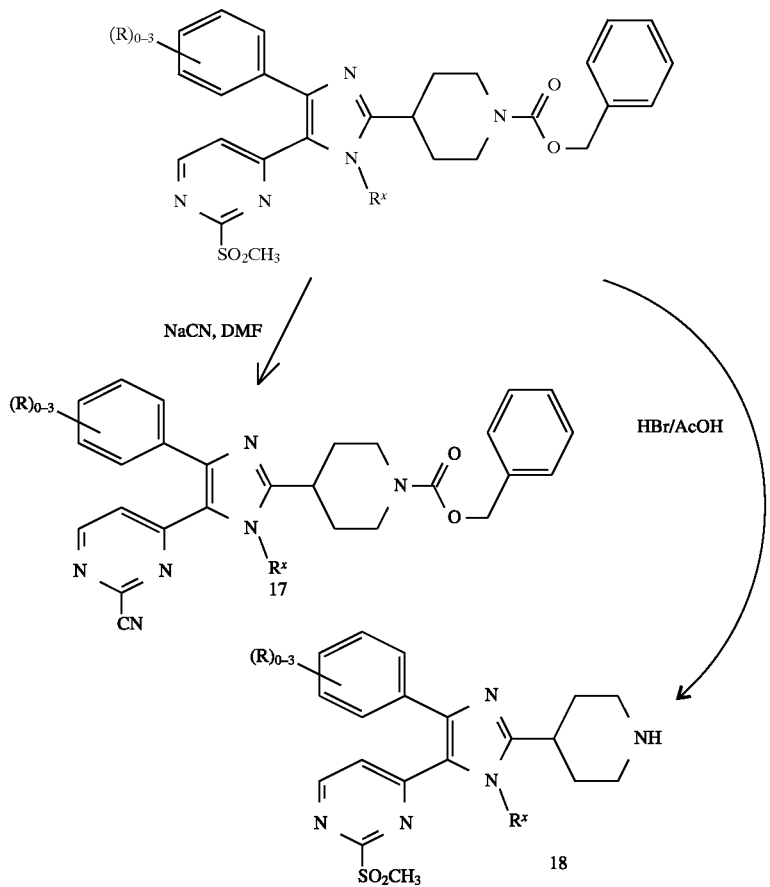

-continued
Scheme 4
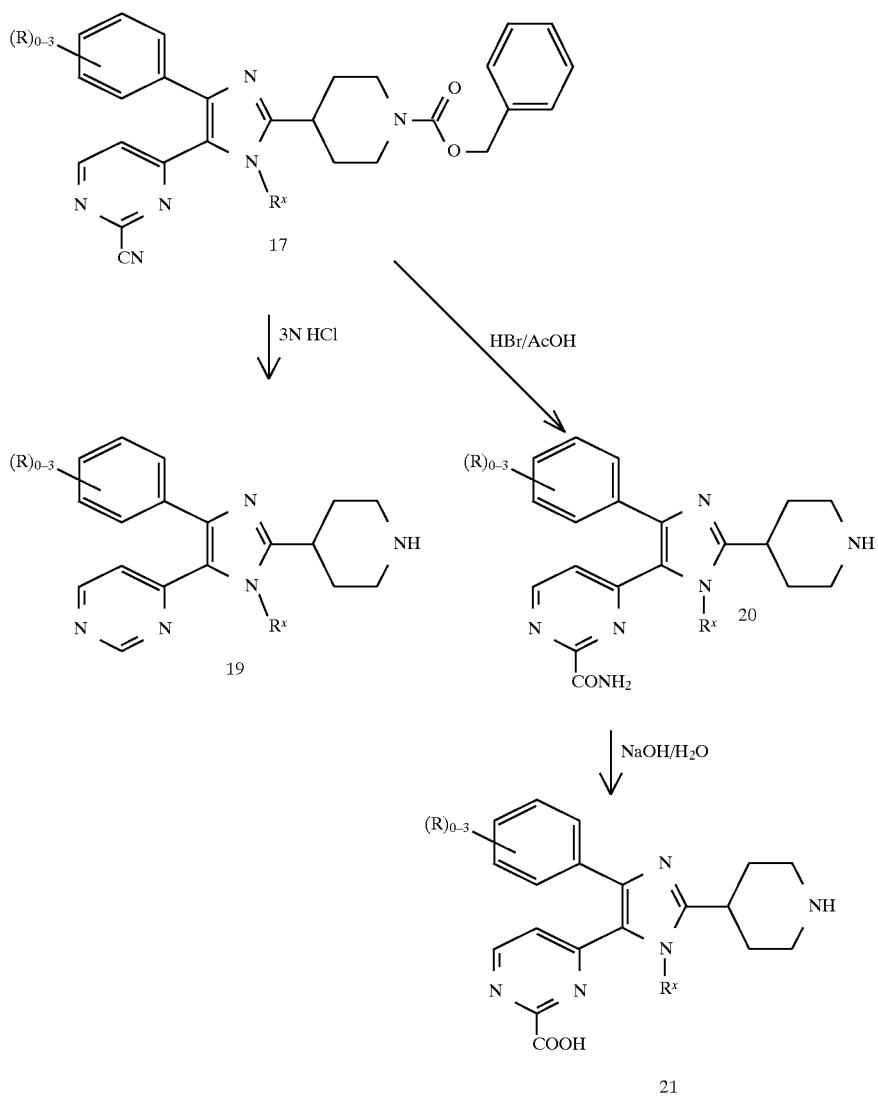
Scheme 5
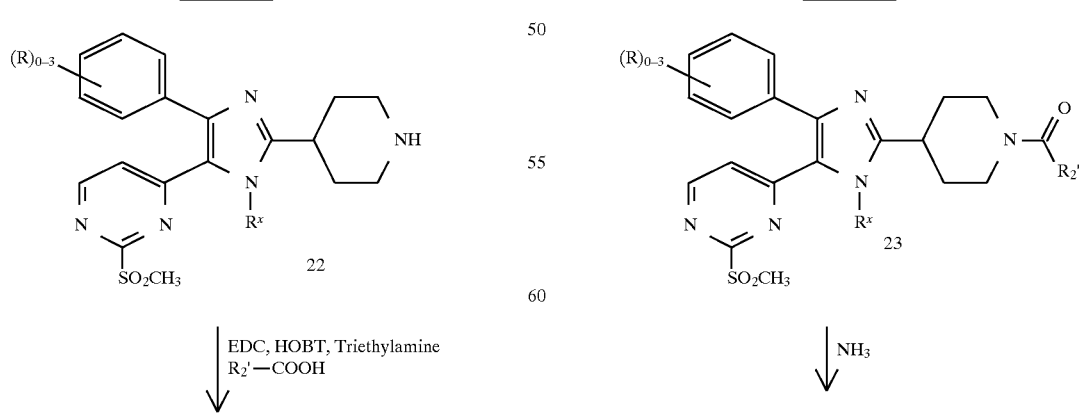

-continued

Scheme 5

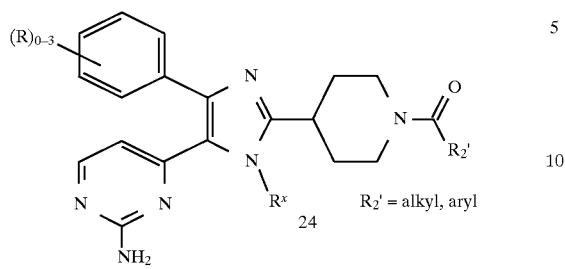

Scheme 6

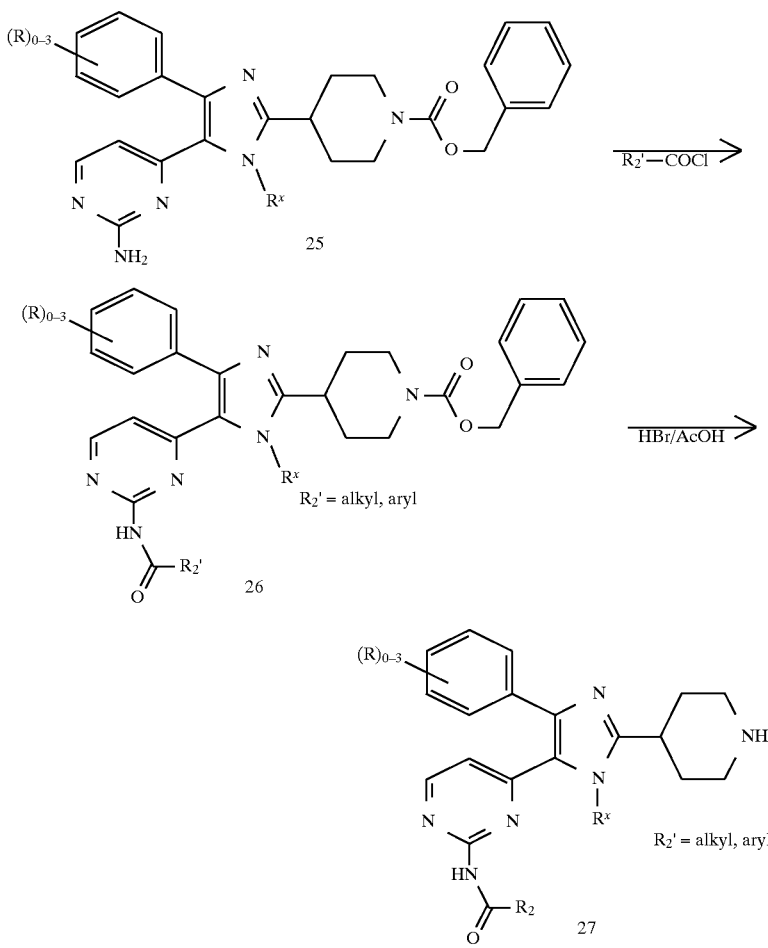

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

The pharmaceutically acceptable salts of the compounds of formula I include conventional non-toxic salts or quarternary ammonium salts of the compounds of formula I formed e.g. from non-toxic inorganic or organic acids. For example, non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methane-sulfonic, ethane disulfonic, oxalic, isethionic, trifluoroacetic and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The compounds of formula 1 can be used in the prophylactic or therapeutic treatment of disease states in mammals which are exacerbated or caused by excessive or unregulated cytokines, e.g., IL- 1, IL-6, IL-8 or TNF.

Because the compounds of formula I inhibit cytokines, the compounds are useful for treating diseases in which cytokine presence or activity is implicated, such as rheumatoid arthritis, rheumatoid spondylitis, osteoarthritis, gouty arthritis and other arthritic conditions.

The compounds of formula I are useful to treat disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation, The compounds of formula I are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound of formula I in an amount which is effective for treating said disease or condition.

When administered to a patient for the treatment of a disease in which a cytokine or cytokines are implicated, the dosage used can be varied within wide limits, depending upon the type of disease, the age and general condition of the patient, the particular compound administered, the presence or level of toxicity or adverse effects experienced with the drug and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

EXAMPLE 1

4-METHOXYBENZYL-[4-[2-PIPERIDIN-4-YL-5-(3-TRIFLUOROMETHYLPHENYL)-3H-IMIDAZOL-4-YL]-PYRIMIDIN-2-YL]AMINE

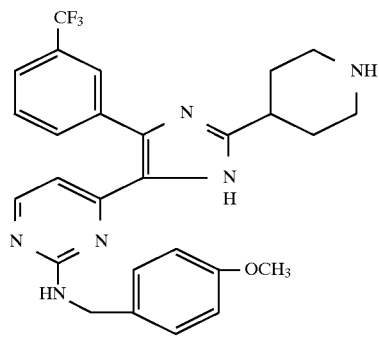

Step 1-A
2-Methylthio-4-methylpyrimidine

To 2-mercapto-4-methylpyrimidine•HCl (50.0 g, 0.307 mole) in toluene (750 mL), under argon, was added diisopropylethylamine (80.0 mL, 0.461 mole) followed by N,N-dimethylformamide dimethyl acetal (100 mL) and the mixture heated to reflux for 4 hours. Upon cooling, the reaction was concentrated in vacuo to an oil, dissolved in ether (400 mL), and washed with water (2×50 mL). The organic extract was dried over anhydrous sodium sulfate, filtered and concentrated to an oil which was vacuum distilled to give 2-methylthio-4-methylpyrimidine (36.4 g) as an oil.

$^1$H NMR(CDCl$_3$) d 8.37 (d, 1 H, J=7.5 Hz), 6.82 (d, 1H, J=7.5 Hz), 2.55 (s 3H), 2.45 (s, 3H).

Step 1-B
2-(2-Methylthiopyrimidin-4-yl)-1-(3-trifluoromethylphenyl)ethanone

To a solution of diisopropylamine (7.9 mL, 0.056 mole) in THF (100 mL) at −78° C. under argon was added 2.5M N-butyllithium (22.5 mL, 0.056 mole), followed after 5 minutes by a solution of 2-methylthio-4-methylpyrimidine (5.27 g, 0.0376 mole) in THF (20 mL). Upon stirring for 15 min. at −78° C., a solution of N-methoxy-N-methyl-3-trifluoromethylbenzamide (9.63 g, 0.041 mole) in THF (90 mL) was added. The reaction was allowed to warm to 0° C. and then quenched by pouring into water (400 mL) and ethyl acetate (400 mL). The layers were separated and the aqueous layer washed with ethyl acetate (200 mL). The ethyl acetate extracts were combined, dried over anhydrous sodium sulfate, filtered, and concentrated to a solid (11.9 g). Trituration with 10% ether/hexane (100 mL) gave 9.5 g of the title compound.

$^1$H NMR (CDCl$_3$) (mixture of keto-and enol tautomers) d 6.0–8.5 (m, 6H, rotamers), 2.4–2.7 (m, 3H).

Step 1-C
1-(2-Methylthiopyrimidin-4-yl)-2-(3-trifluoromethylphenyl)-ethane-1,2-dione 1-oxime To a mixture of 2-(2-methylthiopyrimidin-4-yl)-1-(3-trifluoromethylphenyl)ethanone (4.5 g, 0.0144 mole) in acetic acid (67 mL), was added THF (54 mL) and water (9 mL). The mixture was cooled to +5° C. and a solution of sodium nitrite (1.34 g, 0.0194 mole) added dropwise while maintaining the temperature below +10° C. Upon completion of addition, the reaction was allowed to warm to room temperature for 1 hour, diluted with water (200 mL) and ethyl acetate (200 mL) and the pH adjusted to 7.5 with 3N NaOH. The layers were separated and the aqueous layer washed with ethyl acetate (100 mL). The organic layers were combined, dried over anhydrous sodium sulfate, filtered and concentrated to an oil. Yield 4.9 g.

$^1$H NMR (CDCl$_3$) d 9.58 (d, 1H, J=5.4 Hz), 8.18 (s, 1H), 8.06 (d, 1H, J=8.6 Hz), 7.89 (d, 1H, J=8.6 Hz), 7.66 (t, 1H, J=8.6 Hz), 7.52 (d, 1H, J=5.4 Hz), 2.18 (s, 3H), 1.60 (brs, 1H).

Step 1-D
4-[1-Hydroxy-5-(2-methylthiopyrimidin-4-yl)-4-(3-trifluoromethylphenyl)-1H-imidazol-2-yl]piperidine-1-carboxylic acid benzyl ester To a mixture of 1-(2-methylthiopyrimidin-4-yl)-2-(3-trifluoromethylphenyl)ethane-1,2-dione-1-oxime (5.0 g, 0.0146 mole) and N-carbobenzyloxypiperidine-4-carboxaldehyde [Amici et al Eur. J. Med. Chem. 26, 625–631 (1991)] (4.70 g, 0.019 mole), in acetic acid (140 mL) was added ammonium acetate (23 g, 0.295 mole). The mixture was heated to reflux for 1½ hours, cooled and concentrated to remove most of the acetic acid. The residue was dissolved in water (200 mL) and ethyl acetate (400 mL) and the pH adjusted to 7.5 with 3N sodium hydroxide. The ethyl acetate layer was removed, dried over Na$_2$SO$_4$, filtered and concentrated to give an oil (9.5 g crude product). The oil was used in the next step without further purification.

Step 1-E
4-[5-(2-Methylthiopyrimidin-4-yl)-4-(3-trifluoromethylphenyl)-1H-imidazol-2-yl]piperidine-1-carboxylic acid benzyl ester To a stirring solution of 4-[1-hydroxy-5-(2-methylthiopyrimidin-4-yl)-4-(3-trifluoromethylphenyl)-1H-imidazol-2-yl]piperidine-1-carboxylic acid benzyl ester (9.5 g. crude, 0.0146 mole) in methanol (130 mL) at 20° C. was added titanium (III) chloride (25 mL, 0.029 mole, 15% wt in 20–30% HCl) dropwise over 10 minutes. The reaction was allowed to stir for 3 hours then quenched by pouring slowly into a mixture of 10% aqueous sodium bicarbonate (1.5 L) and ethyl acetate (600 mL). After stirring for 30 minutes the organic layer was removed and aqueous extract washed with ethyl acetate (2×200 mL). The organic extracts were combined, dried over anhydrous sodium sulfate, and concentrated to an oil. The oil was chromatographed on silica using 60% ethyl acetate/hexane to give 6.35 g of a yellow foam upon concentration of product containing fractions.

$^1$H NMR (CDCl$_3$) d 10.18 (brs, 1H), 8.28 (d, 1H, J=5.5 Hz), 7.2–7.8 (m, 9H), 6.95 (d, 1H, J=5.5 Hz), 5.12 (s, 2H), 4.30 (brs, 2H), 3.0 (brm, 3H), 2.58 (s, 3H), 1.7–2.2 (m, 4H).

Step 1-F

4-[5-(2-Methylsulfonylpyrimidin-4-yl)-4-(3-trifluoromethylphenyl)-1H-imidazol-2-yl]piperidine-1-carboxylic acid benzyl ester To a stirring solution of 4-[5-(2-methylthiopyrimidin-4-yl)-4-(3-trifluoromethylphenyl)-1H-imidazol-2-yl] piperidine-1-carboxylic acid benzyl ester (2.5 g, 0.0045 mole) in methanol (75 mL) at 20° C. was slowly added an aqueous solution (75 mL) of Oxone® (8.32 g, 0.0135 mole). The reaction was allowed to stir for 4 hours, concentrated in vacuo to remove methanol, diluted with 10% aqueous sodium bicarbonate (100 mL), and extracted with ethyl acetate (2×150 mL). The organic extracts were combined, dried over anhydrous sodium sulfate, filtered and concentrated to give the title compound (2.75 g).

$^1$H NMR (CDCl$_3$) d 11.06 (s,1H), 7.5–8.6 (m, 6H), 7.35 (m, 5H), 5.12 (s, 2H), 4.30 (brs, 2H), 3.35 (s, 3H), 2.7–3.1 (m, 3H), 1.8–2.2 (m, 4H).

Step 1-G

4-[5-(2-(4-Methoxybenzylamino)-pyrimidin-4-yl)-4-(3-trifluoromethylphenyl)-1H-imidazol-2-yl]-piperidine-1-carboxylic acid benzyl ester A mixture of 4-[5-(2-methylsulfonylpyrimidin-4-yl)-4-(3-trifluoromethylphenyl)-1H-imidazol-2-yl]-piperidine-1-carboxylic acid benzyl ester (1.5 g, 0.00256 mole) and 4-methoxybenzylamine (3.51 g, 0.026 mole) was heated in a pressure tube at 140° C. for 10 minutes. The mixture was allowed to cool and the residue column chromatographed on silica using 5% methanol/methylene chloride to give 1.52 g of a yellow powder upon concentration in vacuo of product containing fractions.

Anal. Calc'd for $C_{35}H_{33}N_6O_3F_3$: C 65.41, H 5.18, N 13.08. Found: C 65.12, H 5.29, N 12.98.

Step 1-H

4-Methoxybenzyl-[4-[2-piperidin-4-yl-5-(3-trifluoromethylphenyl)-3H-imidazol-4-yl]-pyrimidin-2-yl] amine To a stirred solution of 4-[5-[2-(4-methoxybenzylamino)-pyrimidin-4-yl]-4-(3-trifluoromethylphenyl)-1H-imidazol-2-yl]-piperidine-1-carboxylic acid benzyl ester (1.0 g, 0.00156 mole) in methylene chloride (16 mL) under argon was slowly added 30% hydrogen bromide in acetic acid (16 mL). The mixture was stirred at 20° C. for 30 minutes and then diluted with diethyl ether (160 mL). The resulting mixture was stirred for I hour, filtered and solid washed with ether (10 mL). The resulting solid was dissolved in 10% aqueous sodium bicarbonate (40 mL) and methylene chloride (50 mL). The methylene chloride was separated and the aqueous layer washed with methylene chloride (25 mL). The organic extracts were dried over anhydrous sodium sulfate, filtered and concentrated to a foam (0.80 g). The solid was chromatographed on silica using methylene chloride/methanol/aqueous ammonium hydroxide (90:10:2) to give upon concentration of product containing fractions 180 mg of the title compound.

$^1$H NMR (CDCl$_3$) d 9.8 (brs, 1H), 8.12 (d, 1H, J=5.8 Hz), 7.90 (s, 1H), 7.80 (d, 1H, J=8.1 Hz), 7.62 (d, 1H, J=8.1 Hz), 7.42 (t, 1H, J=8.1 Hz), 7.32 (d, 1H, J=8.1 Hz), 6.90 (d, 2H, J=8.1 Hz), 6.78 (brs, 1H), 5.44 (brs, 1H), 4.6 (brs, 2H), 3.80 (s, 3H), 3.22 (m, 2H), 2.95 (m, 1H), 2.77 (m, 2H), 1.6–2.2 (m, 4H).

The following examples (2–17) were prepared as described in Example 1 and were isolated either by silica gel chromatography to give the free base, preparative HPLC to give the trifluoroacetic acid salt upon lyophilization, or crystallization of the hydrobromide salts.

EXAMPLE 2

4-[5-(2-METHYLAMINOPYRIMIDIN-4-YL)-4-(3-TRIFLUOROMETHYLPHENYL)-1H-IMIDAZOL-2-YL]-PIPERIDINE-1-CARBOXYLIC ACID BENZYL ESTER

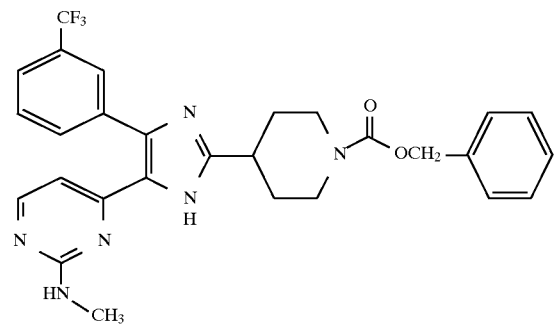

To a stirred solution of 4-[5-(2-methylsulfonylpyrimidin-4-yl)-4-(3-trifluoromethylphenyl)-1H-imidazol-2-yl]-piperidine-1-carboxylic acid benzyl ester (Example 1F) (0.5 g, 0.8 mmole) in ethanol (10 mL) in a pressure vessel (50 mL) was added 40% aqueous methylamine (20 mL). The vessel was sealed and then heated at 100° C. for 3 hours. The reaction was cooled, concentrated in vacuo and chromatographed on silica using methylene chloride/methanol/aqueous ammonium hydroxide (95:5:1) to give 0.42 g of product. Crystallization from ether (15 mL) gave 0.30 g of the title compound as a white solid.

Anal. Calc'd for $C_{28}H_{27}N_6O_2F_3$: C 62.68, H 5.07, N 15.66. Found: C 62.89, H 5.05, N 15.92.

EXAMPLE 3

4-[5-(2-METHYLAMINOPYRIMIDIN-4-YL)-4-(3-TRIFLUOROMETHYLPHENYL)-1H-IMIDAZOL-2-YL]-PIPERIDINE

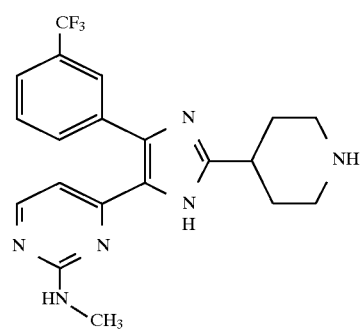

The title compound was prepared from 4-[5-[2-(methylamino)-pyrimidin-4-yl]-4-(3-trifluoromethylphenyl)-1H-imidazol-2-yl]-piperidine-1-carboxylic acid benzyl ester (Example 1F as described in Example 1 step H.

Anal Calc'd for $C_{20}H_{21}N_6F_3$: C 59.69, H 5.26, N 20.88
Found: C 59.62, H 5.31, N 20.95

EXAMPLE 4

4-[5-(2-DIMETHYLAMINOPYRIMIDIN-4-YL)-4-(3-TRIFLUOROMETHYLPHENYL)-1H-IMIDAZOL-2-YL]-PIPERIDINE

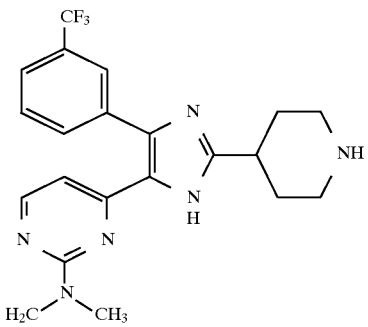

The title compound was prepared in a similar manner from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 steps G (replacing 4-methoxybenzylamine with 40% aqueous dimethylamine) and H.

$^1$H NMR (CDCl$_3$) d 9.9 (brs, 1H), 8.15 (d, 1H, J=5.0 Hz), 7.9 (s, 1H), 7.81 (d, 1H, J=7.4 Hz), 7.62 (d, 1H, J=7.4 Hz), 7.54 (t, 1H, J=7.4 Hz), 6.54 (brs, 1H), 3.2 (m, 6H), 3.0 (m, 1H), 2.78 (m, 2H), 1.7–2.2 (m, 6H).

Mass Spectral Analysis—M$^{+1}$=417.

EXAMPLE 5

4-[5-[2-(1-PIPERDINYL)-PYRIMIDIN-4-YL]-4-(3-TRIFLUOROMETHYLPHENYL)-1H-IMIDAZOL-2-YL]-PIPERIDINE

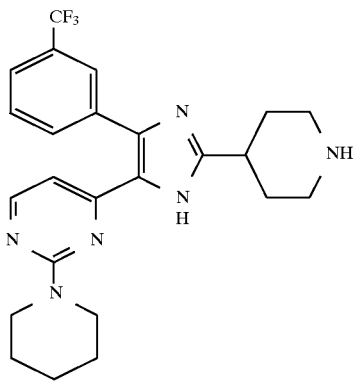

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 steps G (replacing 4-methoxybenzylamine with piperidine) and H.

$^1$H NMR (CDCl$_3$) d 9.8 (brs, 1H), 8.15 (d, 1H, J=5.5 Hz), 7.90 (s, 1H), 7.80 (d, 1H, J=7.8 Hz), 7.62 (d, 1H, J=7.8 Hz), 7.52 (t, 1H, J=7.8 Hz), 3.80 (brs, 4H), 3.22 (m, 2H), 3.0 (m, 1H), 2.77 (m, 2H), 1.4–2.2 (m, 10H).

EXAMPLE 6

(R)-4-[5-(2-(1-PHENYLETHYLAMINO)-PYRIMIDIN-4-YL)-4-(3-TRIFLUOROMETHYLPHENYL)-1H-IMIDAZOL-2-YL]-PIPERIDINE-1-CARBOXYLIC ACID BENZYL ESTER

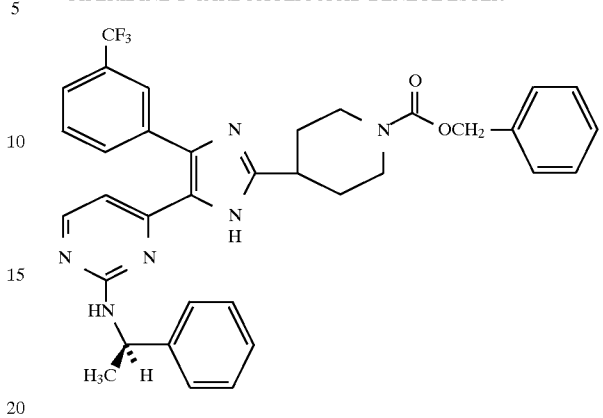

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 steps (replacing 4-methoxybenzylamine with R(+)-a-methylbenzylamine).

Anal. Calc'd for $C_{35}H_{33}N_6O_2F_3 \cdot 0.3H_2O$: C 66.50, H 5.36, N 13.30 Found: C 66.52, H 5.27, N 13.32

MP 85°–87° C.

EXAMPLE 7

(R)-4-[5-(2-(1-PHENYLETHYLAMINO)-PYRIMIDIN-4-YL)-4-(3-TRIFLUOROMETHYLPHENYL)-1H-IMIDAZOL-2-YL]-PIPERIDINE HYDROCHLORIDE

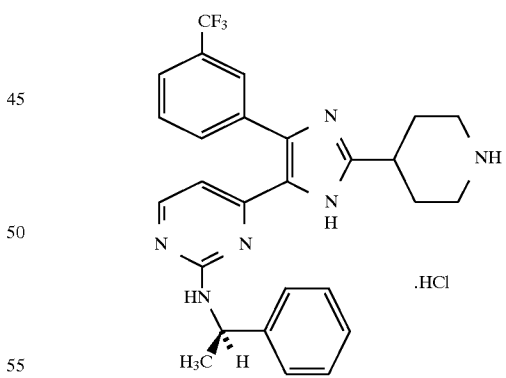

The title compound was prepared from (R)-4-[5-(2-(1-phenylethylamino)-pyrimidin-4-yl)-4-(3-trifluoromethylphenyl)-1H-imidazol-2-yl]-piperidine-1-carboxylic acid benzyl ester (Example 6) as described in Example 1 step H.

MP=155°–160° C. $[a]_D$=+165.1° (MeOH)

EXAMPLE 8

(S)-4-[5-[2-(1-PHENYLETHYLAMINO)-PYRIMIDIN-4-YL]-4-(3-TRIFLUOROMETHYLPHENYL)-1H-IMIDAZOL-2-YL]-PIPERIDINE-1-CARBOXYLIC ACID BENZYL ESTER

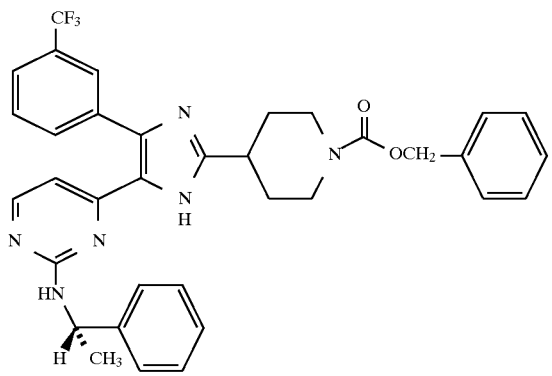

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 step G (replacing 4-methoxybenzylamine with S(−)-a-methylbenzylamine).

Anal. Calc'd for $C_{35}H_{33}N_6O_2F_3 \cdot 0.2H_2O$: C 66.69, H 5.34, N 13.33 Found: C 66.74, H 5.38, N 12.98

MP 85°–87° C.

EXAMPLE 9

(S)-4-[5-(2-(1-PHENYLETHYLAMINO)-PYRIMIDIN-4-YL)-4-(3-TRIFLUOROMETHYLPHENYL)-1H-IMIDAZOL-2-YL]-PIPERIDINE

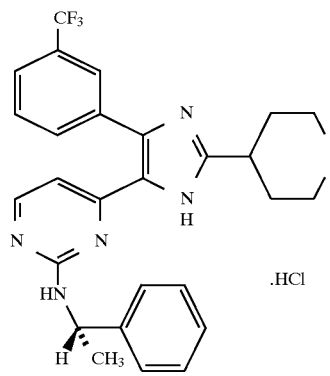

.HCl

The title compound was prepared from (S)-4-[5-[2-(1-phenylethylamino)-pyrimidin-4-yl]-4-(3-trifluoromethylphenyl)-1H-imidazol-2-yl]-piperidine-1-carboxylic acid benzyl ester (Example 8) as described in Example 1 step H.

MP 157°–161° C.

$[a]_D = -165.1°$ (MeOH)

EXAMPLE 10

4-[5-(2-(CYCLOPROPYLAMINO)PYRIMIDIN-4-YL)-4-(3-TRIFLUOROMETHYLPHENYL)-1H-IMIDAZOL-2-YL]-PIPERIDINE-1-CARBOXYLIC ACID BENZYL ESTER

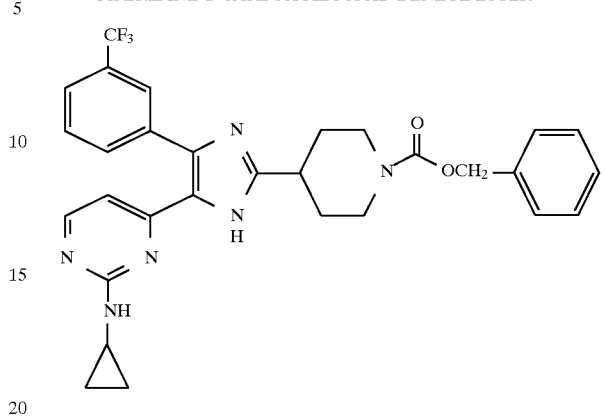

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 step G (replacing 4-methoxybenzylamine with cyclopropylamine).

Mass Spectral Analysis=$M^{+1}$=563.

EXAMPLE 11

4-[5-(2-(CYCLOPROPYLAMINO)PYRIMIDIN-4-YL)-4-(3-TRIFLUOROMETHYLPHENYL)-1H-IMIDAZOL-2-YL]-PIPERIDINE

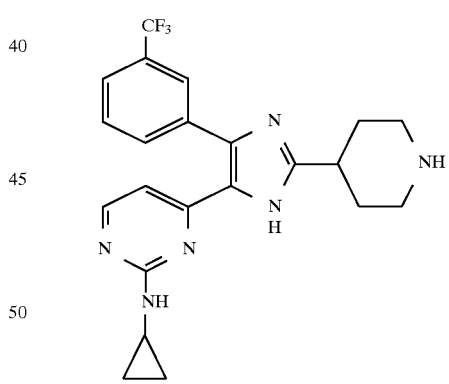

The title compound was prepared 4-[5-(2-(Cyclopropylamino)pyrimidin-4-yl)-4-(3-trifluoromethylphenyl)-1H-imidazol-2-yl]-piperidine-1-carboxylic acid benzyl ester (Example 10) as described in Example 1 step H.

$^1$H NMR(CDCl$_3$) d 10.1 (brs, 1H), 8.16 (d, 1H, J=5.3 Hz), 7.92 (s, 1H), 7.80 (d, 1H, J=8.0 Hz), 7.62 (d, 1H, J=8.0 Hz), 7.54 (t, 1H, J=8.0 Hz), 6.62 (brs, 1H), 3.20 (m, 2H), 3.0 (m, 1H), 2.75 (m, 2H), 1.7–2.2 (m, 5H), 0.5–1.0 (m, 4H).

EXAMPLE 12

4-[5-(2-AMINOPYRIMIDIN-4-YL)-4-(3-TRIFLUOROMETHYLPHENYL)-1H-IMIDAZOL-2-YL]-PIPERIDINE-1-CARBOXYLIC ACID BENZYL ESTER

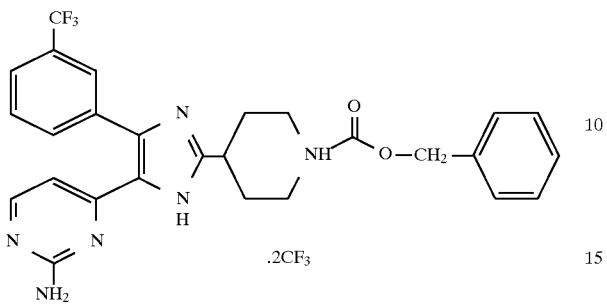

.2CF₃

To a 50 mL pressure vessel cooled to −50° C. and containing 4-[5-(2-methylsulfonylpyrimidin-4-yl)-4-(3-trifluoromethylphtenyl)-1H-imidazol-2-yl]-piperidine-1-carboxylic acid benzyl ester (Example 1F) (100 mg, 0.176 mmole) was introduced liquid ammonia (10 mL). The vessel was sealed, allowed to warm to 25° C. and stirred for 18 hours. The ammonia was allowed to evaporate and the residue purified by preparative HPLC using a C-18 column and 0.1% trifluoroacetic acid/water and acetonitrile as eluants. The title compound was isolated from the product containing fractions by lyophilization to yield 100 mg.

Mass Spectral Analysis—$M^{+1}$=523

Anal. Calc'd for $C_{27}H_{25}N_6O_2F_3 \cdot 2.0CF_3COOH$: C 49.60, H 3.63, N 11.20 Found: C 49.53,H 3.40,N 10.90

EXAMPLE 13

4-[5-(2-(2,2,2-TRIFLUOROETHYLAMINO)-PYRIMIDIN-4-YL)-4-(3-TRIFLUOROMETHYLPHENYL)-1H-IMIDAZOL-2-YL]-PIPERIDINE

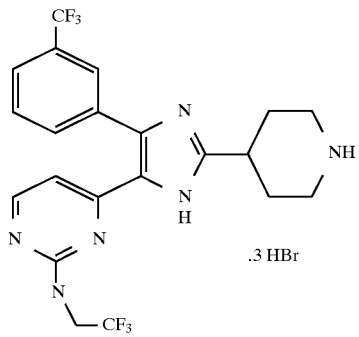

.3 HBr

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 steps G (replacing 4-methoxybenzylamine with 2,2,2-trifluoromethylamine and carrying out the reaction for 7 days at 140° C.) and H.

Mass Spectral Analysis—$M^{+1}$=471

MP—205°–210° C.

EXAMPLE 14

4-TRIFLUOROMETHYLBENZYL-[4-[2-PIPERIDIN-4-YL-5-(3-TRIFLUOROMETHYLPHENYL)-3H-IMIDAZOL-4-YL]-PYRIMIDIN-2-YL]AMINE

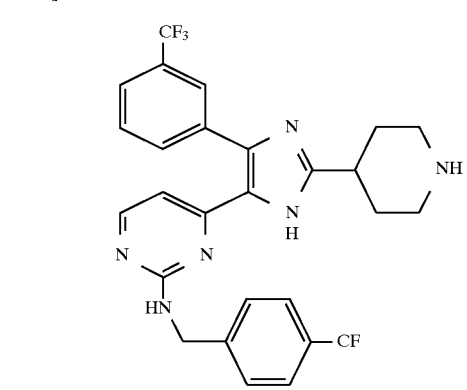

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 steps G (replacing 4-methoxybenzylamine with 4-trifluoromethylbenzylamine) and H. Purification by preparative HPLC resulted in isolation of the trifluoroacetic acid salt after lyophilization of product containing fractions.

Anal Calc'd for $C_{27}H_{24}N_6F_6 \cdot 2.8CF_3COOH$: C 45.22, H 3.12, N 9.71 Found: C 45.48,H 3.22,N 9.83

MP 75°–79° C.

EXAMPLE 15

3-TRIFLUOROMETHYLBENZYL-[4-[2-PIPERIDIN-4-YL-5-(3-TRIFLUOROMETHYLPHENYL)-3H-IMIDAZOL-4-YL]-PYRIMIDIN-2-YL]AMINE

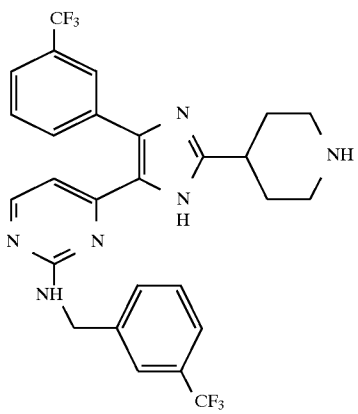

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example IF) as described in Example 1 steps G (replacing 4-methoxybenzylamine with 3-trifluoromethylbenzylamine) and H. Purification by preparative HPLC resulted in isolation of the trifluoroacetic acid salt after lyophilization of product containing fractions.

Anal. Calc'd for $C_{27}H_{24}N_6F_6 \cdot 2.8CF_3COOH$: C 45.22,H 3.12,N 9.71 Found: C 45.31,H 3.24,N 9.71

MP 68°–74° C.

EXAMPLE 16

2-TRIFLUOROMETHYLBENZYL-[4-[2-PIPERIDIN-4-YL-5-(3-TRIFLUOROMETHYLPHENYL)-3H-IMIDAZOL-4-YL]-PYRIMIDIN-2-YL]AMINE

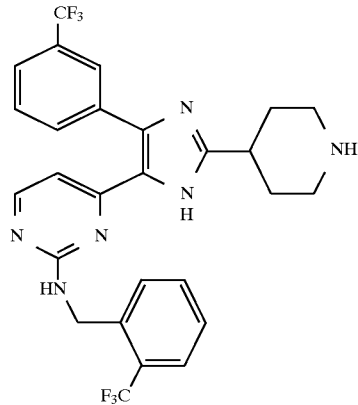

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 steps G (replacing 4-methoxybenzylamine with 2-trifluoromethylbenzylamine) and H. Purification by preparative HPLC resulted in isolation of the trifluoroacetic acid salt after lyophilization of product containing fractions.

Anal. Calc'd for $C_{27}H_{24}N_6F_6 \cdot 3.0CF_3COOH$: C 44.15, H 3.14, N 9.36 Found: C 44.16, H 3.15, N 9.21

MP 65°–68° C.

EXAMPLE 17

4-[5-(2-(2-INDANYLAMINO)-PYRIMIDIN-4-YL)-4-(3-TRIFLUOROMETHYLPHENYL)-1H-IMIDAZOL-2-YL]-PIPERIDINE

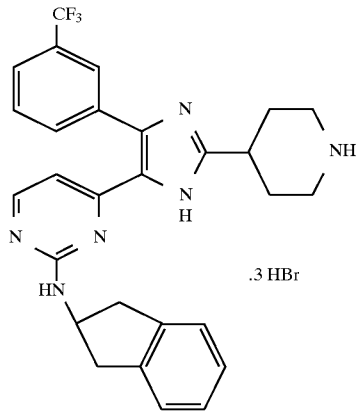

The title compound was prepared from 4-[5-(2-methylsulfonylpyrimidin-4-yl)-4-(3-trifluoromethylphenyl)-1H-imidazol-2-yl]-piperidine-1-carboxylic acid benzyl ester (Example 1F) as described in Example 1 steps G (replacing 4-methoxybenzylamine with 2-aminoindane) and H. The product was isolated as the trihydrobromide salt.

Anal. Calc'd for $C_{28}H_{27}N_6F_3 \cdot 3HBr$, 1.5 $H_2O$: C 43.41, H 4.29, N 10.85 Found: C 43.78, H 4.59, N 10.49

EXAMPLE 18

[4-[2-(1-METHYL-PIPERIDIN-4-YL)-5-(3-TRIFLUOROMETHYLPHENYL)-3H-IMIDAZOL-4-YL]-PYRIMIDIN-2-YL]-4-METHOXYBENZYLAMINE

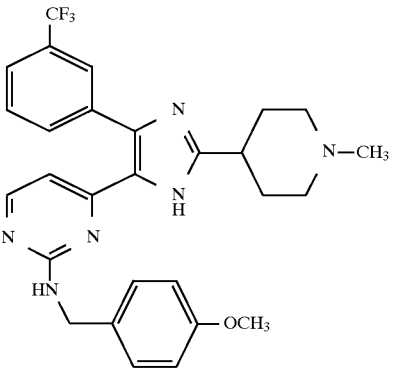

To a stirred solution of 4-[5-(2-(4-methoxybenzylamino)-pyrimidin-4-yl)-4-(3-trifluoromethylphenyl)-1H-imidazol-2-yl]-piperidine-1-carboxylic acid benzyl ester (Example 1G) (0.227 g, 0.000353 mole) in THF (10 mL) was slowly added 1.0M lithium aluminum hydride in THF (0.53 mL, 0.0053 mole). The reaction was warmed to reflux for 30 min., cooled and water (200 mL) added dropwise. The reaction mixture was diluted with THF (20 mL) and sodium sulfate (1.0 g) added. The mixture was stirred well for 10 minutes, filtered, concentrated in vacuo, and chromatographed on silica using methylene chloride/methanol/aqueous ammonium hydroxide (90:10:2) to give 100 mg of the title compound upon concentration of product containing fractions. The residue was triturated from 10% ether/hexane to give 70 mg of the title compound as a white solid.

$^1$H NMR (CDCl$_3$) d 9.85 (brs, 1H), 8.10 (brd, 1H), 7.91 (s, 1H), 7.80 (d, 1H, J=8.1), 7.5–7.7 (m, 2H), 7.31 (d, 2H, J=8.1 Hz), 6.90 (d, 2H, J=8.1), 6.59 (brd, 1H), 5.45 (brs, 1H), 4.58 (d, 2H, J=5.6Hz), 3.80 (s, 3H), 2.8–3.0 (m, 3H), 2.32 (s, 3H), 1.8–2.2 (m, 6H).

Anal Calc'd for $C_{28}H_{29}N_6OF_3 \cdot 0.3 H_2O$: C 63.69, H 5.65, N 15.92 Found: C 63.70, H 5.70, N 15.94

EXAMPLE 19

1-[4-[5-(2-(4-METHOXYBENZYLAMINO)-
PYRIMIDIN-4-YL)-4-(3-
TRIFLUOROMETHYLPHENYL)-
1H-IMIDAZOL-2-YL]-
PIPERIDINE-YL]-ETHANONE

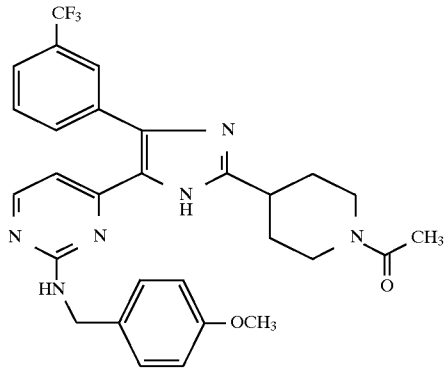

To a stirred solution of 4-methoxybenzyl-[4-[2-piperidin-4-yl-5-(3-trifluoromethylphenyl)-3H-imidazol-4-yl]-pyrimidin-2-yl]amine (Example 1H) (0.150 g, 0.295 mmole) in DMF (4 mL) was added acetic acid (18 mL, 0.31 mmole), triethylamine (62 mL, 0.44 mmole), 1-hydroxybenztriazole hydrate (68 mg, 0.44 mmole) and EDC (85 mg, 0.44 mmole). The mixture was stirred at 20° C. for 18 hours then diluted with 10% aqueous sodium bicarbonate (20 mL) and ethyl acetate (30 mL). The organic extract was removed, washed with water (10 mL), dried over anhydrous sodium sulfate, filtered, and column chromatographed on silica using methylene chloride/methanol/aqueous ammonium hydroxide (95:5:1) to give 146 mg. Crystallization from ether gave 120 mg of the title compound.

Anal Calc'd for $C_{29}H_{29}N_6O_2F_3$: C 63.20, H 5.31, N 15.26
Found: C 62.80, H 5.29, N 15.16

EXAMPLE 20

1-[4-[5-(2-(4-METHOXYBENZYLAMINO)
PYRIMIDIN-4-YL)-4-(3-
TRIFLUOROMETHYLPHENYL)-
1H-IMIDAZOL-2-YL]-PIPERIDINYL]-
2-DIMETHYLAMINOETHANONE

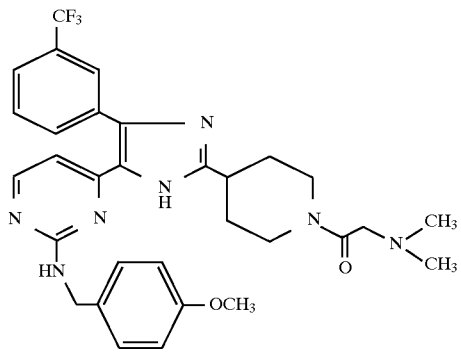

The following compound was prepared from 4-methoxybenzyl-[4-[2-piperidin-4-yl-5-(3-trifluoromethylphenyl)-3H-imidazol-4-yl]-pyrimidin-2-yl]amine (Example 1H) as described in example 19 using N'-N'-dimethylglycine in place of acetic acid to give the title compound.

$^1$H NMR (CDCl$_3$) d 9.78 (brs, 1H), 8.12 (d, 1H, J=5.8 Hz), 7.90 (s, 1H), 7.80 (d, 1H, J=8.1Hz), 7.64 (d, 1H, J=8.1 Hz), 7.54 (t, 1H, J=8.1 Hz), 7.30 (d, 2H, J=8.5 Hz), 6.90 (d, 2H, J=8.5 Hz), 6.58 (d, 1H, J=5.8 Hz), 3.8 (s, 3H), 2.3 (s, 6H).

Anal Calc'd for $C_{31}H_{34}N_7O_2F_3$: C 62.72, H 5.77, N 16.52
Found: C 62.57, H 5.95, N 16.76

EXAMPLE 21

[4-[2-(1-BENZYLPIPERIDIN-4-YL)-5-(3-
TRIFLUOROMETHYLPHENYL)-3H-
IMIDAZOL-4-YL]-PYRIMIDIN-
2-YL]-4-METHOXYBENZYLAMINE.

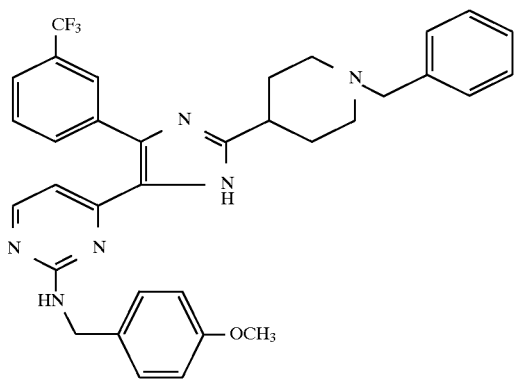

To a well stirred solution of 4-methoxybenzyl-[4-[2-piperidin-4-yl-5-(3-trifluoromethylphenyl)-3H-imidazol-4-yl]-pyrimidin-2-yl]amine (Example 1H) (100 mg, 0.197 mmole) and benzaldehyde (22 mg, 0.21 mmole) in dichloromethane under argon was added sodium triacetoxyborohydride (44 mg, 0.21 mmole). The mixture was stirred for 4 hours and then quenched by addition of 1N HCl (5 mL). Aqueous sodium bicarbonate (20 mL) and ethyl acetate (20 mL) were added and the layers mixed well. The ethyl acetate layer was removed, concentrated in vacuo and residue chromatographed on silica using methylene chloride/methanol/aqueous ammonium hydroxide (97:3:1) to give upon concentration of product containing fractions 94 mg of an oil. Crystallization from ether/hexane (4 mL) gave 80 mg solid.

$^1$H NMR (CDCl$_3$) d 9.75 (brs, 1H), 8.10 (d, 1H, J=5.5 Hz), 7.90 (s, 1H), 7.80 (d, 1H, J=8.7 Hz), 7.62 (d, 1H, J=8.7 Hz), 7.54 (t, 1H, J=8.7 Hz), 7.25–7.4 (m, 7H), 6.90 (d, 2H, J=8.7 Hz), 6.58 (d, 1H, J=5.5 Hz), 4.58 (d, 2H, 6.2 Hz), 3.78 (s, 3H), 3.53 (s, 2H), 3.0 (m, 2H), 2.85 (m, 1H), 1.8–2.2 (m, 6H).

Anal Calc'd for $C_{34}H_{33}N_6OF_3$: C 68.21, H 5.56, N 14.04
Found: C 67.99, H 5.59, N 13.88

EXAMPLE 22

[4-[2-PIPERIDIN-4-YL-5-(3-TRIFLUOROMETHYLPHENYL)-3H-IMIDAZOL-4-YL]-PYRIMIDIN-2-YL]AMINE TRIHYDROCHLORIDE

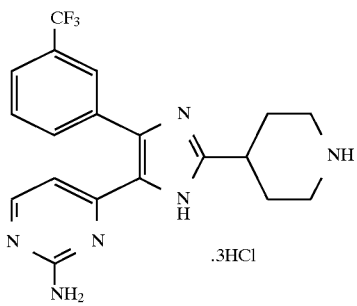

4-Methoxybenzyl-[4-[2-piperidin-4-yl-5-(3-trifluoromethylphenyl)-3H-imidazol-4-yl]pyrimidin-2-yl]amine (Example 1H) (0.125 mg, 0.26 mmole) and 3N HCl (35 mL) were heated to 100° C. for 12 hours. The reaction was cooled, washed with diethyl ether (10 mL), and concentrated in vacuo to a solid. Trituration from 80% ether/ethanol (10 mL) gave the title compound, 0.102 g, as a yellow solid.

MP—225°–230° C.

$^1$H NMR (CD$_3$OD) d 8.19 (d, 1H, J=6.6Hz), 8.0 (s, 1H), 7.96 (d, 1H, J =8.4 Hz), 7.89 (d, 1H, J=8.4 Hz), 7.77 (t, 1H, J=8.4 Hz), 7.02 (d, 1H, J =6.6 Hz), 3.2–3.6 (m, 5H), 2.1=2.4 (m, 4H).

EXAMPLE 23

4-[5-(2-AMINOPYRIMIDIN-4-YL)-1-METHYL-4-(3-TRIFLUOROMETHYLPHENYL)-1H-IMIDAZOL-2-YL]-PIPERIDINE-1-CARBOXYLIC ACID BENZYL ESTER

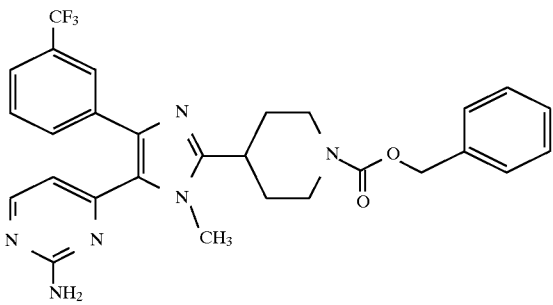

Step 23A
4-[5-(2-Methylthiopyrimidin-4-yl)-1-methyl-4-(3-trifluoromethylphenyl)-1H-imidazol-2-yl]-piperidine-1-carboxylic acid benzyl ester To a stirring solution of 4-[5-(2-methylthiopyrimidin-4-yl)-4-(3-trifluoromethylphenyl)-1H-imidazol-2-yl]-piperidine-1-carboxylic acid benzyl ester (Example 1E) (4.0 g, 7.22 mmole) in toluene (80 mL) was added dimethylformamide dimethyl acetal (4.0 mL) and the mixture heated to reflux for 18 hours. The reaction was cooled, concentrated in vacuo to a foam and chromatographed on silica using 5% acetone/methylene chloride to give upon concentration of the product containing fractions the title compound 2.78 g.

$^1$H NMR (CDCl$_3$) d 8.33 (d, 1H, J=6.0 Hz), 7.78 (s, 1H), 7.5–7.6 (m, 2H), 7.3–7.45 (m, 6H):, 6.76 (d, 1H, J=6.0 Hz), 5.13 (s, 2H), 4.35 (brs, 2H), 3.80 (S, 3H), 2.98 (m, 3H), 2.60 (s, 3H), 2.0 (m, 4H).

Additional elution of the above column chromatography with 5% methanol/methylene chloride gave 4-[4-(2-methylthiopyrimidin-4-yl)-1-methyl-5-(3-trifluoromethylphenyl)-1H-imidazol-2-yl]-piperidine-1-carboxylic acid benzyl ester.

$^1$H NMR (CDCl$_3$) d 8.39 (d, 1H, J=6.0 Hz), 7.5–7.74 (m, 5H), 7.3–7.44 (m, 5H), 5.18 (S, 2H), 4.35 (brs, 2H), 3.38 (s, 3H), 2.7–3.1 (m, 3H), 1.9–2.1 (m, 4H), 1.7 (S, 3H).

Step 23B
4-[5-(2-Methylsulfonylpyrimidin-4-yl)-1-methyl-4-(3-trifluoromethylphenyl)-1H-imidazol-2-yl]-piperidine-1-carboxylic acid benzyl ester The title compound was prepared by oxidation of 4-[5-(2-methylthiopyrimidin-4-yl)-1-methyl-4-(3-trifluoromethylphenyl)-1H-imidazol-2-yl]-piperidine-1-carboxylic acid benzyl ester as described in Example 1 step F.

$^1$H NMR (CDCl$_3$) d 8.58 (d, 1H, J=5.7 Hz), 7.76 (S, 1H), 7.60 (m, 2H, J=10.0 Hz), 7.48 (t, 1H, J=10.0 Hz), 7.37 (m, 5H), 7.24 (d, 1H, J=5.7 Hz), 5.14 (S, 2H), 4.34 (brs, 2H), 3.98 (S, 3H), 3.40 (S, 3H), 3.01 (m, 3H), 1.90–2.0 (m, 4H).

Step 23C
4-[5-(2-Aminopyrimidin-4-yl)-1-methyl-4-(3-trifluoromethylphenyl)-1 H-imidazol-2-yl]-piperidine-1-carboxylic acid benzyl ester The title compound was prepared from 4-[5-(2-Methylsulfonylpyrimidin-4-yl)-1-methyl-4-(3-trifluoromethylphenyl)-1H-imidazol-2-yl]-piperidine-1-carboxylic acid benzyl ester as described in Example 12.

MP—80°–83° C.

Mass Spectral Analysis—M$^{+1}$=537

$^1$H NMR (CDCl$_3$) d 8.18 (d, 1H, J=5.9 Hz), 7.82 (S, 1H), 7.61 (d, 1H, J =8.6 Hz), 7.49 (d, 1 H, J=8.6 Hz), 7.3–7.4 (m, 6H), 6.48 (d, 1 H, J=5.9 Hz), 5.1–5.3 (m, 4H), 4.35 (brs, 2H), 3.74 (S, 3H), 2.95 (m, 3H), 1.8–2.1 (m, 4H).

EXAMPLE 24

4-[5-(2-AMINOPYRIMIDIN-4-YL)-1-METHYL-4-(3-TRIFLUOROMETHYLPHENYL)-1H-IMIDAZOL-2-YL]-PIPERIDINE

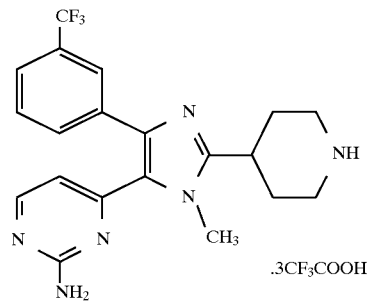

The title compound was prepared from 4-[4-(2-Aminopyrimidin-4-yl)-1-methyl-4-(3-trifluoromethylphenyl)-1H-imidazol-2-yl]-piperidine-1-carboxylic acid benzyl ester as described in Example 1 step H, and isolated as the trifluoroacetic acid salt after purification by preparative HPLC and lyophilization of the product containing fractions.

MP=57°–60° C.

$^1$H NMR (CD$_3$OD) 8.06 (d,1H, J=6.5 Hz), 7.84 (s, 1H), 7.72 (m, 2H), 7.62 (t, 1H, J=8.1 Hz), 6.53 (d, 1H, J=6.5Hz), 4.00 (s, 3H), 3.2–3.4 (m, 5H), 2.0–2.2 (m, 4H)

Mass Spectral Analysis—M$^{+1}$=403

EXAMPLE 25

4-[4-(2-AMINOPYRIMIDIN-4-YL)-1-METHYL-5-(3-TRIFLUOROMETHYLPHENYL)-3H-IMIDAZOL-2-YL]PIPERIDINE-1-CARBOXYLIC ACID BENZYL ESTER

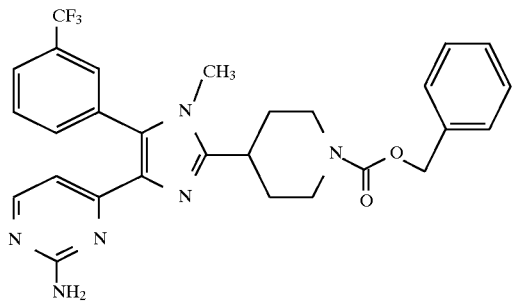

The title compound was prepared from 4-[4-(2-methylthiopyrimidin-4-yl)-1-methyl-5-(3-trifluoromethylphenyl)-3H-imidazol-2-yl]piperidine-1-carboxylic acid benzyl ester as described in Example 12.

MP 215°–217° C.

Anal Calc'd for $C_{28}H_{27}N_6O_2F_3$: C 62.68, H 5.07, N 15.66
Found: C 62.34, H 4.77, N 15.50

Mass Spectral Analysis—$M^{+1}$=537

EXAMPLE 26

4-[4-(2-AMINOPYRIMIDIN-4-YL)-1-METHYL-5-(3-TRIFLUOROMETHYLPHENYL)-3H-IMIDAZOL-2-YL]-PIPERIDINE

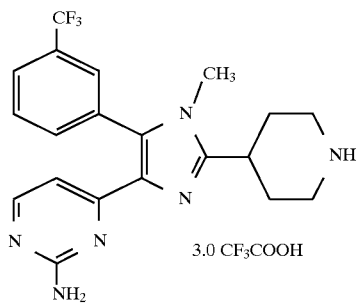

3.0 CF₃COOH

The title compound was prepared from 4-[4-(2-aminopyrimidin-4-yl)-1-methyl-5-(3-trifluoromethylphenyl)-3H-imidazol-2-yl]-piperidine-1-carboxylic acid benzyl ester as described in Example I step H.

Mass Spectral Analysis—$M^{+1}$=403.

EXAMPLE 27

4-{[2-PIPERIDIN-4-YL]-5-(3-TRIFLUOROMETHYLPHENYL)-3H-IMIDAZOL-4-YL}-PYRIMIDINE-2-CARBOXAMIDE TRIHYDROBROMIDE

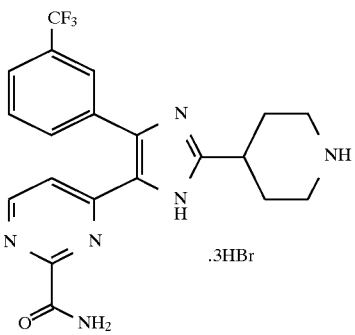

.3HBr

Step 27A
4-[5-[2-Cyanopyrimidin-4-yl]-4-(3-trifluoromethyl)-1H-imidazol-2-yl]-piperidine-1-carboxylic acid benzyl ester.

To a stirred solution of 4-[5-(2-methylsulfonylpyrimidin-4-yl)-4-(3-trifluoromethylphenyl)-1H-imidazol-2-yl]-piperidine-1-carboxylic acid benzyl ester (Example 1F) (0.50 g, 0.85 mmole) in dimethyl sulfoxide (3 mL) was added sodium cyanide (0.087 g, 1.70 mmole) and the resulting mixture warmed to 60° C. for 2 hours. The reaction was cooled, diluted with water (30 mL) and extracted with ethyl acetate (2×30 mL). The ethyl acetate extracts were dried over anhydrous sodium sulfate, filtered and concentrated to an oil. The residue was chromatographed on silica using ethyl acetate/hexane to give upon concentration of the product containing fractions a foam, (0.455 g).

Mass Spectral Analysis—$M^{+1}$=533.

Step 27B
4-[2-Piperidin-4-yl]-5-(3-trifluoromethylphenyl)-3H-imidazol-4-yl)-pyrimidine-2-carboxamide trihydrobromide The title compound was prepared from 4-[5-[2-cyanopyrimidin-4-yl]-4-(3-trifluoromethyl)-1H-imidazol-2-yl]-piperidine-1-carboxylic acid benzyl ester as described in Example 1 step H.

Mass Spectral Analysis—$M^{+1}$=417
MP—235°–240° C.

EXAMPLE 28

4-[(2-PIPERIDIN-4-YL)-5-(3-TRIFLUOROMETHYLPHENYL)-3H-IMIDAZOL-4-YL)]-PYRIMIDINE

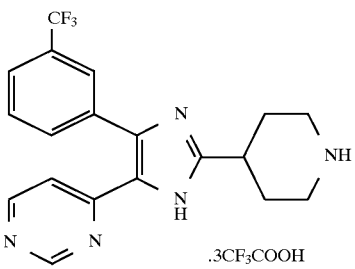

.3CF₃COOH

4-[5-[2-Cyanopyrimidin-4-yl]-4-(3-trifluoromethyl)-1H-imidazol-2-yl]-piperidine-1-carboxylic acid benzyl ester (0.05 g, 0.09 mmole) and 3N HCl (3 mL) were heated to 100° C. for 72 hours. The reaction was cooled and concentrated to a solid. The solid was purified by preparative HPLC to give the title compound (40 mg) upon lyophilization of the product containing fractions.

Mass Spectral Analysis—M$^{+1}$=374.

EXAMPLE 29

4-{[2-PIPERIDIN-4-YL)-5-(3-TRIFLUOROMETHYLPHENYL)-3H-IMIDAZOL-4-YL]}-PYRIMIDIN-2-CARBOXYLIC ACID

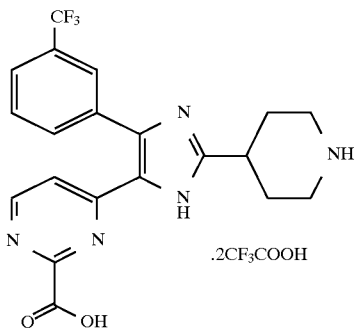

To a stirred solution of 4-{[2-piperidin-4-yl]-5-(3-trifluoromethylphenyl)-3H-imidazol-4-yl)}pyrimidine-2-carboxamide trihydrobromide (0.120 g, 0.18 mmole) in methanol (1 mL) was added 5N sodium hydroxide (1 mL) and the reaction stirred for 18 hours. The reaction was diluted with 5N HCl (1 mL) and purified by preparative HPLC to give the title compound (100 mg) upon lyophilization of the product containing fractions.

Mass Spectral Analysis—M$^{+1}$=418
MP 60°–67° C.

EXAMPLE 30

1-[4-[5-(2-AMINOPYRIMIDIN-4-YL)-4-(3-TRIFLUOROMETHYLPHENYL)-1H-IMIDAZOL-2-YL]-PIPERIDIN-4-YL]ETHANONE

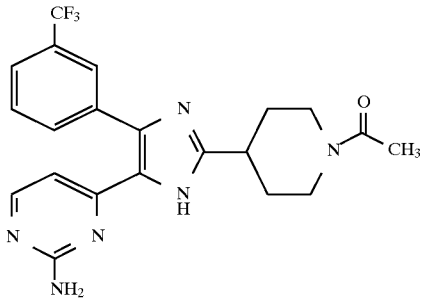

Step 30A
4-[5-(2-Methylsulfonylpyrimidin-4-yl)-4-(3-trifluoromethylphenyl)-1H-imidazol-2-yl]piperidine To a stirred solution of 4-[5-[2-methylsulfonylpyrimidin-4-yl]-4-(3-trifluoromethylphenyl)-1H-imidazol-2-yl]piperidine-1-carboxylic acid benzyl ester (Example 1F) (400 mg, 0.683 mmole) in methylene chloride (6 mL), under argon was added dropwise 30% hydrogen bromide/acetic acid (6.0 mL). The reaction was allowed to stir for 1 hour, diluted with diethyl ether (60 mL) and the resulting solid filtered to give 0.474 g of the dihydrobromide salt.

MP 125°–130° C.
Mass Spectral Analysis—M$^{+1}$=452.
Step 30B
1-[4-[5-(2-Methylsulfonylpyrimidin-4-yl)-4-(3-trifluoromethylphenyl)-1H-imidazol-2-yl]-piperidin-4-yl]ethanone The title compound was prepared from 4-[5-(2-methylsulfonylpyrimidin-4-yl)-4-(3-trifluoromethylphenyl)-1H-imidazol-2-yl]piperidine as described in Example 19.

$^1$H NMR (CD$_3$OD) Rotamer d 8.6–8.84 (brm, 1H), 7.6–8.2 (m, 5H), 4.60 (brd, 1H, J=18 Hz), 4.10 (d, 1H, J=18 Hz), 2.7–3.4 (m, 6H), 2.26 (s, 3H), 1.8–2.2 (m, 4H).

Step 30C

1-[4-[5-(2-Aminopyrimidin-4-yl)-4-(3-trifluoromethylphenyl)-1H-imidazol-2-yl]piperidin-4-yl]ethanone The title compound was prepared from 1-[4-[5-(2-methylsulfonylpyrimidin-4-yl)-4-(3-trifluoromethylphenyl)-1H-imidazol-2-yl]piperidin-4-yl]ethanone described in Example 12.

$^1$H NMR (CD$_3$OD) d 8.14 (d, 1H, J=6.6 Hz), 7.94 (s, 1H), 7.91 (d, 1H, J=8.5 Hz), 7.83 (d, 1H, J=8.5 Hz), 7.73 (t, 1H, J=8.5 Hz), 6.94 (d, 1H, J=6.6Hz), 4.65 (d, 1H, J=18Hz), 4.10 (d, 1H, J=18 Hz), 2.80 (m, 1H), 1.8–2.2 (m, 7H).

Anal Calc'd for C$_{21}$H$_{21}$N$_6$OF$_3$~2.0 CF$_3$COOH•1.0 H$_2$O: C 44.37, H 3.72, N 12.42 Found: C 44.16, H 3.51, N 12.53

EXAMPLE 31

[4-[5-(2-AMINOPYRIMIDIN-4-YL)-4-(3-TRIFLUOROMETHYLPHENYL)-1H-IMIDAZOL-2-YL]-PIPERIDIN-1-YL]PHENYLMETHANONE

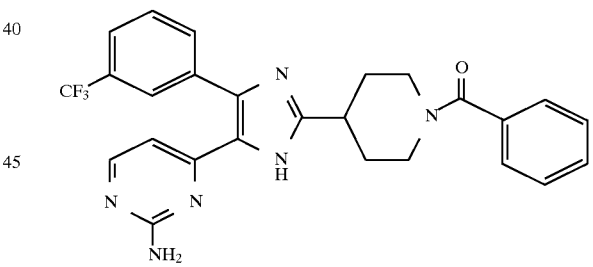

The title compound was prepared from 4-[5-(2-methylsulfonylpyrimidin-4-yl)-4-(3-trifluoromethylphenyl)-1H-imidazol-2-yl]piperidine (Example 30A) as described in Examples 19 (replacing acetic acid with benzoic acid) and 12

$^1$H NMR (CD$_3$OD) d 8.14 (d, 1H, J=6.5 Hz), 7.95 (s, 1H), 7.92 (d, 1H, J=8.7 Hz), 7.84 (d, 1H, J=8.7 Hz), 7.73 (t, 1H, J=8.7 Hz), 7.4–7.6 (m, 5H), 6.96 (d, 1H, J=6.5 Hz), 3.85 (brm, 1H), 3.05 (m, 1H), 1.8–2.2 (m, 6H).

Anal Calc'd for C$_{26}$H$_{23}$N$_6$OF$_3$•2CF$_3$COOH, 0.5H$_2$O: C 49.28,H 3.54,N 11.84 Found: C 49.38,H 3.59, N 11.52

EXAMPLE 32

N-{[5-(2-PIPERIDIN-4-YL)-4-(3-TRIFLUOROMETHYLPHENYL)-1H-IMIDAZOL-4-YL]PYRIMIDIN-2-YL]}ACETAMIDE

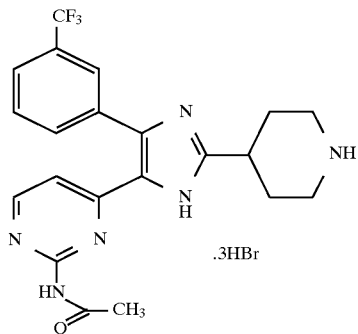

Step 32A

4-[5-(2-Acetamidopyrimidin-4-yl)-4-(3-trifluoromethylphenyl)-1H-imidazol-2-yl]piperidine-1-carboxylic acid benzyl ester To a stirred solution of 4-[5-(2-aminopyrimidin-4-yl)-4-(3-trifluoromethylphenyl)-1H-imidazol-2-yl]-piperidine-1-carboxylic acid benzyl ester (Example 12) (0.220 g, 0.421 mmole) in THF (4 mL) under argon at 0° C. was added diisopropylethylamine (0.22 mL, 1.26 mmole) followed by acetyl chloride (0.036 mL, 0.50 mmole). The reaction was stirred at 20° C. for 1 hour, diluted with water (10 mL) and product extracted with ethyl acetate (2×50 mL). The ethyl acetate extracts were dried over anhydrous sodium sulfate, filtered, concentrated and chromatographed on silica using 5% methanol/methylene chloride to give the product (0.170 g) as an oil.

$^1$H NMR (CDCl$_3$) Rotamers d 10.2 (brs, 1H), 8.56 (d, 1H, J=6.6 Hz), 7.2–8.0 (m, 10H), 5.12 (brs, 2H), 4.30 (brs, 2H), 2.9–3.1 (m, 3H), 2.32 (s, 3H), 1.8–2.2 (m, 5H).

Example 32B

N-[5-(2-Piperidin-4-yl)-4-(3-trifluoromethylphenyl)-1H-imidazol-4-yl]pyrimidin-2-yl]acetamide The title compound was prepared from 4-[5-(2-acetamidopyrimidin-4-yl)-4-(3-trifluoromethyphenyl)-1H-imidazol-2-yl]piperidine-1-carboxylic acid benzyl ester as described in Example 30, Step A.

Mass Spectral Analysis M$^{+1}$=431

MP >200° C. (Dec)

EXAMPLE 33

N-{4-(2-PIPERIDIN-4-YL)-5-(3-TRIFLUOROMETHYLPHENYL)-1H-IMIDAZOL-4-YL]-PYRIMIDIN-2-YL}BENZAMIDE

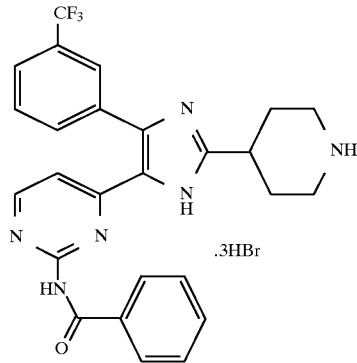

The title compound was prepared from 4-[5-(2-aminopyrimidin-4-yl)-4-(3-trifluoromethylphenyl)-1H-imidazol-2-yl]-piperidine-1-carboxylic acid benzyl ester as described in Example 32 (replacing acetyl chloride with) benzoyl chloride.

MP >260° C. (Dec)

Mass Spectral Analysis—M$^{+1}$=493

EXAMPLE 34

(S)-{4-[3-METHYL-2-PIPERIDIN-4-YL-5-(3-TRIFLUOROMETHYLPHENYL)-3H-IMIDAZOL-4-YL]-PYRIMIDIN-2-YL}-(1-PHENYLETHYL)AMINE

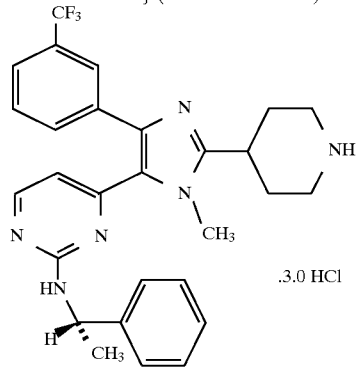

STEP 34A
4-[5-(2-Methylsulfonylpyrimidin-4-yl)-1-methyl-4-(3-trifluoromethylphenyl)-1H-imidazol-2-yl]-piperidine-1-carboxylic acid benzyl ester The title compound was prepared using the procedure set forth in Example 1, Steps 1A to 1E, and Example 23, Steps 23A and 23B.

STEP 34B
(S)-4-[5-(2-(1-Phenylethylamino)pyrimidin-4-yl)-1-methyl-4-(3-trifluoromethylphenyl)-1H-imidazol-2-yl]-piperidine-1-carboxylic acid benzyl ester A mixture of 4-[5-(2-methylsulfonylpyrimidin-4-yl)-1-methyl-4-(3-trifluoromethylphenyl)-1H-imidazol-2-yl]-piperidine-1-carboxylic acid benzyl ester (12.6 gm, 0.021 mole) and S(−)-(a)-methylbenzylamine (25.0 gm, 0.21 mole) was heated to 100° C. for 1 hour, under argon. The mixture was cooled and chromatographed on silica (1 kg) using 40% ethyl acetate/hexane to give (S)-4-[5-[2-(1- phenylethylamino)-pyrimidin-4-yl]-1-methyl-4-(3-trifluoromethylphenyl)-1H-imidazol-2-yl]-piperidine-1-carboxylic acid benzyl ester (13.4 gms.)

STEP34C (S)-4-[5-(2-(1-Phenylethylamino)-pyrimidin-4-yl)-1-methyl-4-(3-trifluoromethylphenyl)-1H-imidazol-2-yl] piperidine To a solution of (S)-4-[5-[2-(1-phenylethylamino)-pyrimidin-4-yl]-1-methyl-4-(3-trifluoromethylphenyl)-1H-imidazol-2-yl]-piperidine-1-carboxylic acid benzyl ester (12.5 gm, 0.0195 mole) in dichloromethane (170 mL) at 0° C., under argon, was slowly added 30% hydrogen bromide in acetic acid (170 mL). The solution was allowed to stir for 1.5 h at 0° C. and then diluted with diethyl ether (2.0 L). The resulting solid was filtered under argon, washed with diethyl ether (500 ml) and sucked dry under argon. The solid was then dissolved in dichloromethane (500 mL) and 10% aqueous sodium bicarbonate (500 mL) and mixed well. The dicholormethane solution was removed and the aqueous layer washed with dichloromethane (200 mL). The dichloromethane extracts were dried over anhydrous sodium sulfate, concentrated and the resulting foam (9.6 gm) chromatographed on silica using (dichloromethane/methanol/acetic acid/water—90/10/1/1). The resulting product containing fractions were washed with 10% aqueous sodium bicarbonate, dried over anhydrous sodium sulfate and concentrated to give (S)-4-[5-[2-(1-phenylethylamino)-pyrimidin-4-yl]-1-methyl-4-(3-trifluoromethylphenyl)-1H-imidazol-2-yl]-piperidine (9.4 gm). The solid was dissolved in ethyl acetate (400 ml) filtered and then treated with a solution of hydrochloric acid/ethyl acetate (84 mL, 0.033 gm HCl/mL, 4 eq.). The resulting solid was filtered, dissolved in water (100 ml) and lyophilized to give (S)-4-[5-[2-(1-phenylethylamino)-pyrimidin-4-yl]-1-methyl-4-(3-trifluoromethylphenyl)-1H-imidazol-2-yl]-piperidine trihydrochloride (12.0 gm).

Anal. Calc. for $C_{28}H_{29}N_6F_3 \cdot 3.0HCl \; 2.7 \; H_2O$. C, 50.57; H, 5.60; N, 12.57 Found C, 50.39; H, 5.47; N, 12.33

$^1$H NMR (CD$_3$OD) d 8.27 (brs, 1H,), 8.0 (s, 1H), 7.91 (d, 1H, J=8.7 Hz), 7.82 (d, 1H, J=8.7 Hz), 7.73 (t, 1H, J=8.7 Hz), 7.2–7.6 (m, 5H), 6.64 (d, 1H, J=6.5 Hz), 5.2 (brs, 1H), 3.2–4.0 (m, 8H), 2.2–2.4 (m, 4H), 1.65 (d, 3H, J=7.2 Hz).

EXAMPLE 35

(S)-{4-[3-METHYL-2-(1-METHYLPIPERIDIN-4-YL)-5-(3-TRIFLUOROMETHYLPHENYL)-3H-IMIDAZOL-4-YL]-PYRIMIDINE-2-YL}-(1-PHENYLETHYL)AMINE

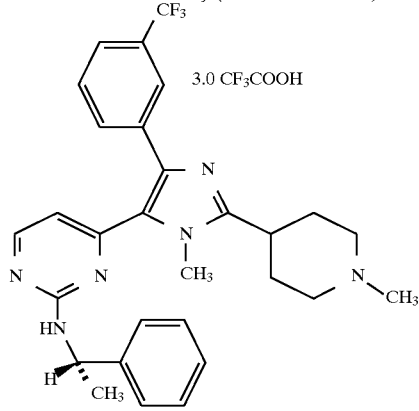

The title compound was prepared from (S)-4-[5-(2-(1-phenylethylamino)pyrimidin-4-yl]-1-methyl-4-(3-trifluoromethylphenyl)-1H-imidazol-2-yl]-piperidine-1-carboxylic acid benzyl ester as described in example 18.

Anal. Calc'd for $C_{29}H_{31}N_6F_3 \; 3CF_3COOH$: C 48.73, H 3.97, N 9.74 Found: C 48.92, H 4.20, N 9.85

EXAMPLE 36

CYCLOPROPYL-{4-[3-METHYL-2-(PIPERIDIN-4-YL)-5-(3-TRIFLUOROMETHYLPHENYL)-3H-IMIDAZOL-4-YL]-PYRIMIDIN-2-YL}AMINE

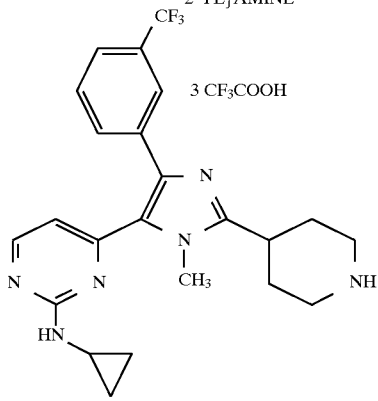

The title compound was prepared from 4-[5-(2-methylsulfonylpyrimidin-4-yl)-1-methyl-4-(3-trifluoromethylphenyl)-1H-imidazol-2-yl]-piperidine-1-carboxylic acid benzyl ester (example 23, step B) as described in example 34, steps B (replacing S(−)-(a)-methylbenzylamine with cyclopropylamine) and C.

Anal Calc'd $C_{23}H_{25}N_6F_3 \; 3.0 \; CF_3COOH \; 1.0 \; H_2O$: C 43.40, H 3.77, N 10.47 Found: C 43.41, H 3.74, N 10.53

EXAMPLE 37

(S)-{4-[3-METHYL-2-(1-CYCLOPROPYLPIPERIDIN-4-YL)-5-(3-TRIFLUOROMETHYL PHENYL)-3H-IMIDAZOL-4-YL]-PYRIMIDINE-2-YL}-(1-PHENYLETHYL)AMINE

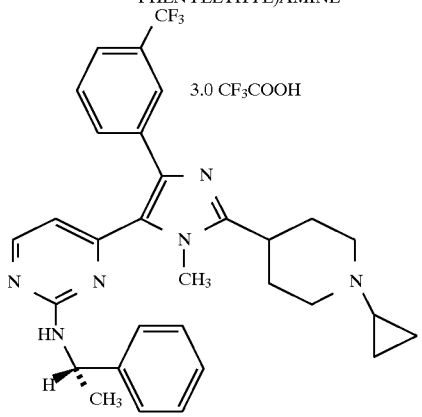

To a solution of (S)-{4-[3-methyl-2-piperidin-4-yl-5-(3-trifluoromethylphenyl)-3H-imidazol-4-yl]-pyrimidin-2-yl}-(1-phenylethyl)amine (300 mg, 0.592 mmole) in methanol (5 ml) under argon was added acetic acid (0.34 ml, 6.0 mmole) and [(1-ethoxycyclopropyl)oxy]-trimethylsilane (0.6 ml, 3.0 mmole). After stirring for 5 minutes sodium cyanoborohydride (150 mg, 2.30 mmole) was added. The mixture was warmed to reflux for 4 hours cooled and concentrated to an oil. The oil was dissolved in methylene chloride (30 ml) and water (20 ml) added. The pH was adjusted to 10.0 with 1N sodium hydroxide and the methylene chloride layer removed, dried over sodium sulfate and concentrated to a foam. The foam was purified by reverse phase preparative HPLC chromatography using 0.1% trifluoroacetic acid/water and acetonitrile to give upon lyophilization of the product containing fractions 480 mg of the title compound.

Anal Calc'd for $C_{31}H_{33}N_6F_3$ 3.0 $CF_3COOH$: C 50.00, H 4.08, N 9.46 Found: C 50.39, H 4.24, N 9.76

EXAMPLE 38

(S)-{4-[2-(1-CYCLOPROPYLMETHYL-[PIPERIDIN-4-YL])-3-METHYL-5-(3-TRIFLUOROMETHYLPHENYL)-3H-IMIDAZOL-4-YL]-PYRIMIDIN-2-YL}-(1-PHENYLETHYL)-AMINE TRIHYDROCHLORIDE

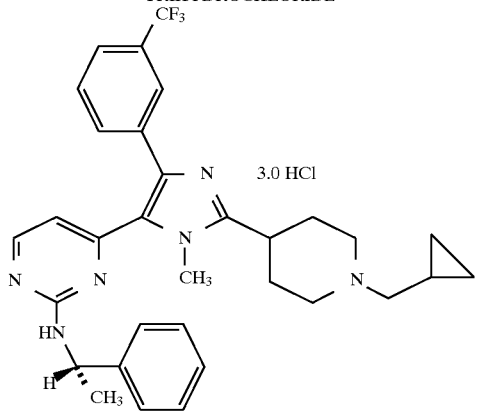

The title compound was prepared from (S)-{4-[3-methyl-2-piperidin-4-yl-5-(3-trifluoromethylphenyl)-3H-imidazol-4-yl]-pyrimidin-2-yl}-(1-phenylethyl)amine (example 34) as described in example 21 (replacing benzaldehyde with cyclopropanecarboxaldehyde).

Anal Calc'd for $C_{32}H_{35}N_6F_3$ 3.0HCl 2.55 $H_2O$: C 53.68, H 6.07, N 11.74 Found: C 53.79, H 6.24, N 11.34

M.P. 145°–155° C.

EXAMPLE 39

(S)-(1-PHENYLETHYL)-{4-[2-PIPERIDIN-4-YL-3-PROPYL-5-(3-TRIFLUOROMETHYLPHENYL)-3H-IMIDAZOL-4-YL]-PYRIMDIN-2-YL}AMINE TRIHYDROCHLORIDE

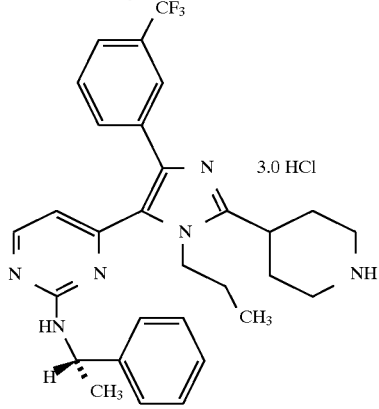

The title compound was prepared using the procedures set forth in Example 1, Steps 1A to 1E, Example 23, Steps 23A (replacing dimethylformamide dimethyl acetal with dimethylformamide dipropyl acetal) and 23B and Example 34, Steps 34B and 34C.

Anal Calc'd for $C_{30}H_{33}N_6F_3$·3.0HCl 0.7 $H_2O$: C 54.87, H 5.74, N 12.80 Found: C 54.92, H 5.98, N 12.55

EXAMPLE 40

{4-[5-(3,4-DICHLOROPHENYL)-3-METHYL-2-PIPERIDIN-4-YL-3H-IMIDAZOL-4-YL]-PYRIMIDIN-2-YL}-(1-PHENYLETHYL)-AMINE

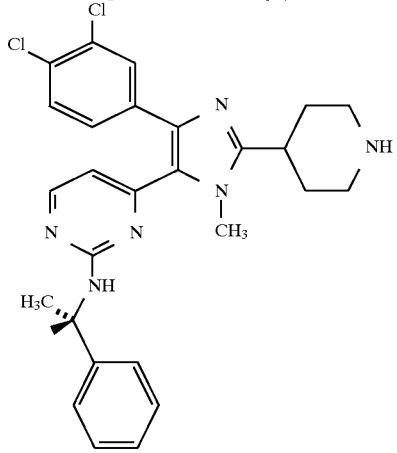

The title compound was prepared using the procedures set forth in Example 1, Steps 1A to 1E (replacing N-methoxy-N-methyl-3-trifluoromethylbenzamide with N-methoxy-N-methyl-3,4-dichlorobenzamide), Example 23, Steps 23A and 23B and Example 34, Steps 34B and 34C.

Anal Calc'd for $C_{27}H_{28}N_6Cl_2$0.6 $CH_3Cl_2$: C 59.36, H 5.27, N 15.05 Found: C 15.52, H 5.07, N 15.03

EXAMPLE 41

{4-[5-(3,4-DICHLOROPHENYL)-3-METHYL-2-PIPERIDIN-4-YL-3H-IMIDAZOL-4-YL]-PYRIMIDIN-2-YL}-(4-METHOXYBENZYL)-AMINE

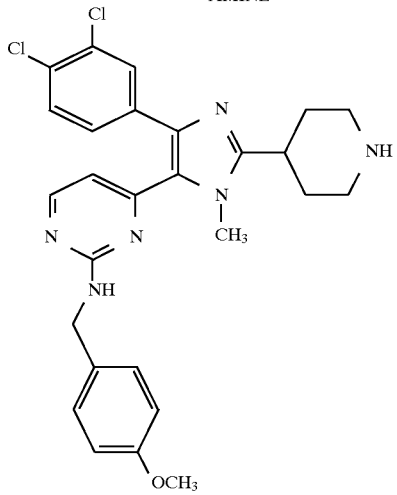

The title compound was prepared using the procedures set forth in Example 1, Steps 1A to 1E (replacing N-methoxy-N-methyl-3-trifluoromethylbenzamide with N-methoxy-N-methyl-3,4-dichlorobenzamide), Example 23, Steps 23A and 23B and Example 34, Steps 34B (replacing S-(a)-methylbenzylamine with 4-methoxybenzylamine) and 34C.

Anal Calc'd for $C_{27}H_{28}N_6Cl_2O$•0.60 $CH_2Cl_2$: C 57.71, H 5.12, N 14.63 Found: C 57.90, H 5.24, N 14.36

EXAMPLE 42

{4-[5-(3,4-DICHLOROPHENYL)-3-PROPYL-2-PIPERIDIN-4-YL-3H-IMIDAZOLE-4-YL]PYRIMIDIN-2-YL}-(1-PHENYLETHYL)-AMINE

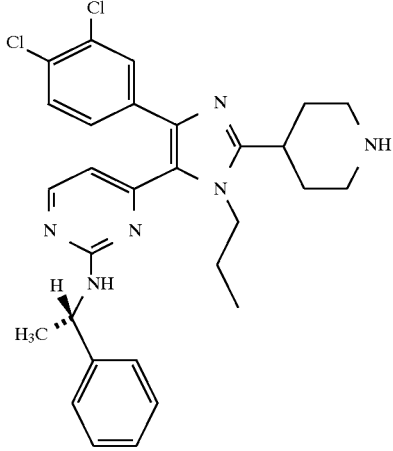

The title compound was prepared using the procedures set forth in Example 1, Steps 1A to 1E (replacing N-methoxy-N-methyl-3-trifluoromethylbenzamide with N-methoxy-N-methyl-3,4-dichlorobenzamide), Example 23, Steps 23A (replacing dimethylformamide dimethyl acetal with dimethylformamide dipropyl acetal) and 23B and Example 34, Steps 34B and 34C.

$^1$H NMR (CDCl$_3$): d (8.14, J=5.13Hz, d, 1H); (7.64, s, 1H); (7.19–7.40, m, 8H); (6.37, J=4.88Hz, d, 1H); (5.78, bs, 1H); (5.21, J=6.84Hz, 13.92, q, 1H); 3.91–4.08, bm, 1H); (3.60–3.78, m, 3H); (3.47, J=6.6Hz, q, 1H); (3.30–3.36, m, 2H); (2.78–2.86, m, 3H); (1.86–1.98, m, 2H); (1.58, J=6.84, Hz d, 3H); (1.00–1.53, m, 3H); (0.60, bs,2H).

EXAMPLE 43

CYCLOPROPYL-{4-[5-(3,4-DICHLOROPHENYL)-2-PIPERIDIN-4-YL-3-PROPYL-3H-IMIDAZOL-4-YL]-PYRIMIDIN-2-YL}-AMINE

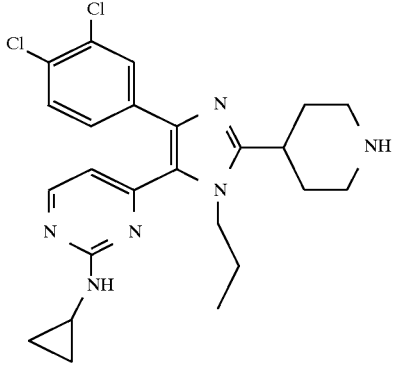

The title compound was prepared using the procedures set forth in Example 1, Steps 1A to 1E (replacing N-methoxy-N-methyl-3-trifluoromethylbenzamide with N-methoxy-N-methyl-3,4-dichlorobenzamide), Example 23, Steps 23A (replacing dimethylformamide dimethyl acetal with dimethylformamide dipropyl acetal) and 23B and Example 34, Steps 34B (replacing S-(a)-methylbenzylamine with cyclopropylamine) and 34C.

$^1$H NMR (CDCl$_3$): d (8.19, J=4.64Hz, bd, 1H); (7.68, s, 1H); (7.24–7.33, b, 2H); (6.44, J=5.12Hz, bd, 1H); (5.47, s, 1H); (4.26, bs, 2H); (3.30, J=12.69Hz, bd, 2H); (2.76–2.88, m, 4H); (2.56, bs, 2H); (1.88–2.17, m, 4H); (1.57–1.64, m, 2H); (1.25, s, 1H); (0.83–0.98, m, 2H); (0.60–0.66, bs, 2H).

EXAMPLE 44

CYCLOHEXYL-{4-[5-(3,4-DICHLOROPHENYL)-2-PIPERIDIN-4-YL-3-PROPYL-3H-IMIDAZOL-4-YL]-PYRIMIDIN-2-YL}-AMINE

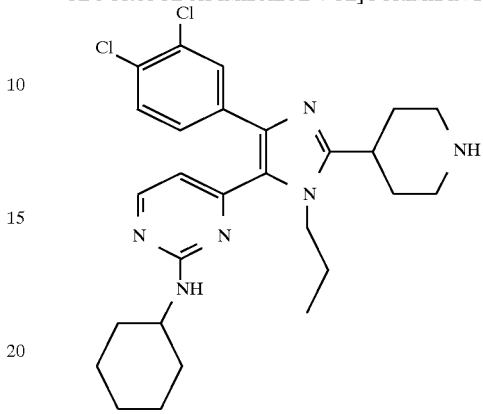

The title compound was prepared using the procedures set forth in Example 1, Steps 1A to 1E (replacing N-methoxy-N-methyl-3-trifluoromethylbenzamide with N-methoxy-N-methyl-3,4-dichlorobenzamide), Example 23, Steps 23A (replacing dimethylformamide dimethyl acetal with dimethylformamide dipropyl acetal) and 23B and Example 34, Steps 34B (replacing S-(a)-methylbenzylamine with cyclohexylamine) and 34C.

$^1$H NMR (CDCl$_3$): d (8.14, J=4.88 Hz, bd, 1H); (7.63, s, 1H); (7.23–7.32, m, 2H); (6.35, J=6.1 Hz, d, 1H); (5.13, J=7.81 Hz, bd, 1H); (4.14–4.19, m, 2H); (3.81–3.91, m, 1H); (3.32, J=12.7 Hz, bd, 2H); (2.71–2.97, m, 4H); (2.17, s, 2H); (1.01–2.17, m, 15H); (0.90–0.99, m, 3H).

The ability of compounds of the present invention to inhibit the synthesis or the activity of cytokines can be demonstrated using the following in vitro assays.

Lipopolysaccharide mediated production of cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium- heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of 2×10$^6$ cell/mL in RPMI containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 hours. at 37° C. in 5% CO$_2$. At the end of the culture period, cell culture supernatants are assayed for IL-1b, TNF-a, IL-6 and PGE$_2$ production using specific ELISA.

IL-1 mediated cytokine production

Human peripheral blood mononuclear cells are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium- heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPMI containing 10% fresh autologous human serum, penicillin streptomycin (10 U/mL) and 0.05% DMSO. Endotoxin free recombinant human IL-1b is then added to a final concentration of 50 pMolar. An aliquot (0.1 mL) of the cells is quickly dispensed into each well of a 96 well plate containing 0.1 mL of the compound at the appropriate dilution. and are incubated for 24 hours. at 37° C. in 5% $CO_2$. At the end of the culture period, cell culture supernatants are assayed for TNF-a, IL-6 and $PGE_2$ synthesis using specific ELISA.

Determination of IL-1b, TNF-a, IL-6 and prostanoid production from LPS or IL-1 stimulated PBMC's IL-1b ELISA Human IL-1b can be detected in cell-culture supernatants or whole blood with the following specific trapping ELISA. Ninety-six well plastic plates (Immulon 4; Dynatech) are coated for 12 hours at 4° C. with 1 mg/mL protein-A affinity chromatography purified mouse anti-human IL-1b monoclonal antibody (purchased as an ascites preparation from LAO Enterprise, Gaithersburg Md.) diluted in Dulbecco's phosphate-buffered saline (—$MgCl_2$, —$CaCl_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1b standards are prepared from purified recombinant IL-1b produced from E. coli. The highest concentration begins at 10 ng/mL followed by 11 two-fold serial dilutions. For detection of IL-1b from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1b polyclonal antisera diluted 1:500 in PBS-Tween is added to the plate and incubated for 1 hour at room temperature followed by six washes with PBS-Tween. Detection of bound rabbit anti-IL-1b IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-a ELISA

Immulon 4 (Dynatech) 96-well plastic plates are coated with a 0.5 mg/mL solution of mouse anti-human TNF-a monoclonal antibody. The secondary antibody is a 1:2500 dilution of a rabbit anti-human TNF-a polyclonal serum purchased from Genzyme. All other operations are identical to those described above for IL-lb. The standards are prepared in PBS-Tween+10% FBS or HS. Eleven 2 fold dilutions are made beginning at 20 ng/mL TNF-a.

IL-6 ELISA

Levels of secreted human IL-6 are also determined by specific trapping ELISA as described previously in Chin and Kostura, J. Immunol. 151, 5574–5585 (1993). (Dynatech) ELISA plates are coated with mouse anti-human IL-6 monoclonal antibody diluted to 0.5 mg/mL in PBS. The secondary antibody, a rabbit anti-human IL-6 polyclonal antiserum, is diluted 1:5000 with PBS-Tween. All other operations are identical to those described above for IL-1b. The standards are prepared in PBS-Tween+10% FBS or HS. Eleven 2 fold dilutions are made beginning at 50 ng/mL IL-6.

$PGE_2$ production

Prostaglandin E2 is detected in cell culture supernatants from LPS or IL-1 stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wash.) are maintained in culture medium supplemented with 15% fetal bovine serum and 1% CS-HBGF consisting of aFGF and heparin. The cells are then diluted 20-fold before being plated (250 µl) into gelatin coated 96-well plates. Prior to use, culture medium is replaced with fresh medium (200 µl). Buffer or test compound (25µl, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/mL) of multiple samples based on the standard curve. IC50 values where appropriate are generated by non-linear regression analysis.

What is claimed is:

1. A compound represented by formula I:

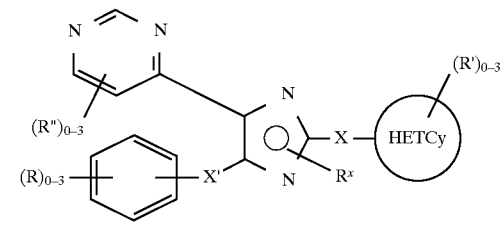

or a pharmaceutically acceptable salt thereof, wherein:

X and X' each independently represent —$(CH_2)_m$—Y—$(CH_2)_n$—, wherein m and n represent integers within the range of from 0–4, such that the sum of m and n is from 0–6; Y represents a member selected from the group consisting of: a direct bond; O; $S(O)_y$, with y equal to 0, 1 or 2; $NR^q$, with $R^q$ as defined below; C(O); OC(O); C(O)O; $SO_xNR^q$ with x equal to 1 or 2 and $R^q$ as defined below; $NR^qSO_x$; $C(O)NR^q$ and $NR^qC(O)$;

represents a 4 to 10 membered non-aromatic heterocycle containing at least one N atom, and optionally containing 1–2 additional N atoms and 0–1 O or S atom;

$R^x$ represents H, $C_{1-6}$ alkyl$(R^q)_3$, $C_{3-8}$ cycloalkyl, $OC_{1-6}$ alkyl$(R^q)_3$ or $C(O)C_{1-6}$ alkyl$(R^q)_3$;

each R independently represents a member selected from the group consisting of: halo; hydroxy; $C_{1-6}$ alkyl$(R^q)_3$; $OC_{1-6}$ alkyl$(R^q)_3$; $C_{3-8}$ cycloalkyl$(R^q)_3$; CN; $CONH_2$;

CONHC$_{1-6}$ alkyl(R$^q$)$_3$; CON(C$_{1-6}$alkyl(R$^q$)$_3$)$_2$; NH$_2$; NHC$_{1-6}$alkyl(R$^q$)$_3$; NHC$_{3-8}$ cycloalkyl; N(C$_{1-6}$ alkyl (R$^q$)$_3$)$_2$; CON(C$_{3-8}$ cycloalkyl)(C$_{1-6}$ alkyl(R$^q$)$_3$)); CO$_2$H; CO$_2$C$_{1-6}$ alkyl(R$^q$)$_3$; C(O)C$_{1-6}$ alkyl(R$^q$)$_3$; aryl (R$^q$)$_3$; heterocyclyl(R$^q$)$_3$; heteroaryl(R$^q$)$_3$; CF$_3$; SH; NO$_2$; NHSO$_2$C$_{1-6}$alkyl(R$^q$)$_3$, NHSO$_2$aryl(R$^q$)$_3$, NHSO$_2$heteroaryl(R$^q$)$_3$; N(R$^{q'}$)C(O)C$_{1-6}$ alkyl(R$^q$)$_3$; NR$^{q'}$C(O)NH(C$_{1-6}$ alkyl(R$^q$)$_3$); C$_{2-4}$ alkenyl(R$^q$)$_{2-3}$ and C$_{2-4}$ alkynyl(R$^q$)$_{1-3}$;

each R" independently represents a member selected from the group consisting of: halo; hydroxy; C$_{1-6}$ alkyl(R$^q$)$_3$; OC$_{1-6}$ alkyl(R$^q$)$_3$; C$_{3-8}$ cycloalkyl(R$^q$)$_3$; CN; CONH$_2$; CONHC$_{1-6}$ alkyl(R$^q$)$_3$; CON(C$_{1-6}$alkyl(R$^q$)$_3$)$_2$; NH$_2$; NHC$_{1-6}$alkyl(R$^q$)$_3$; NHC$_{3-8}$ cycloalkyl; N(C$_{1-6}$ alkyl (R$^q$)$_3$)$_2$; CON(C$_{3-8}$ cycloalkyl)(C$_{1-6}$ alkyl(R$^q$)$_3$)); CO$_2$H; CO$_2$C$_{1-6}$ alkyl(R$^q$)$_3$; C(O)C$_{1-6}$alkyl(R$^q$)$_3$; aryl (R$^q$)$_3$; heterocyclyl(R$^q$)$_3$; heteroaryl(R$^q$)$_3$; CF$_3$; SH; NO$_2$; SO$_y$C$_{1-6}$ alkyl(R$^q$)$_3$, with y as defined above; SO$_2$NH$_2$; SO$_2$NHC$_{1-6}$ alkyl(R$^q$)$_3$; SO$_2$N(C$_{1-6}$alkyl(R$^q$)$_3$)$_2$; NHSO$_2$C$_{1-6}$alkyl(R$^q$)$_3$, NHSO$_2$aryl(R$^q$)$_3$, NHSO$_2$heteroaryl(R$^q$)$_3$; N(R$^{q'}$)C(O)C$_{1-6}$ alkyl(R$^q$)$_3$; NR$^{q'}$C(O)NH(C$_{1-6}$ alkyl(R$^q$)$_3$); C$_{2-4}$ alkenyl(R$^q$)$_{2-3}$ and C$_{2-4}$ alkynyl(R$^q$)$_{1-3}$;

each R' independently represents a member selected from the group consisting of: CONH$_2$; CONHC$_{1-6}$ alkyl(R$^q$)$_3$; CON(C$_{1-6}$ alkyl(R$^q$)$_3$)$_2$; CONHC$_{3-8}$ cycloalkyl(R$^q$)$_3$; CON(C$_{3-8}$ cycloalkyl(R$^q$)$_3$)$_2$; CON(C$_{3-8}$ cycloalkyl)(C$_{1-6}$ alkyl(R$^q$)$_3$)); CO$_2$H; CO$_2$C$_{1-6}$ alkyl(R$^q$)$_3$; C(O) C$_{1-6}$ alkyl(R$^q$)$_3$; CO$_2$C$_{3-8}$ cycloalkyl(R$^q$)$_3$; C(O)C$_{3-8}$ cycloalkyl(R$^q$)$_3$; —[C(O)(CH$_2$)$_j$—CR$^5$R$^6$—(CH$_2$)$_k$— NR$^7$]$_p$—R$^8$; —C(O)C$_{3-8}$ cycloalkyl(R$^q$)$_3$; —C(O) heterocyclyl(R$^q$)$_3$, —CON[C$_{1-6}$alkyl(R$^q$)$_3$][C$_{3-8}$ cycloalkyl(R$^q$)$_3$]; —C(O)aryl(R$^q$)$_3$; —C(O)heteroaryl (R$^q$)$_3$; hydroxy; C$_{1-6}$alkyl(R$^q$)$_3$; C$_{3-8}$ cycloalkyl(R$^q$)$_3$; OC$_{1-6}$ alkyl(R$^q$)$_3$; OC$_{3-8}$ cycloalkyl(R$^q$)$_3$; heterocyclyl (R$^q$)$_3$; CN; NH(R$^{q'}$); NHC$_{1-6}$ alkyl(R$^q$)$_3$; N(C$_{1-6}$ alkyl (R$^q$)$_3$)$_2$; NHC$_{3-8}$ cycloalkyl(R$^q$)$_3$; N(C$_{3-8}$ cycloalkyl (R$^q$)$_3$)$_2$; CF$_3$; SH; NO$_2$; C$_{2-4}$ alkenyl(R$^q$)$_{2-3}$, aryl(R$^q$)$_3$; heteroaryl(R$^q$)$_3$; C$_{2-4}$ alkynyl(R$^q$)$_{1-3}$; —OC(O) C$_{3-8}$ cycloalkyl(R$^q$)$_3$; SO$_2$NH$_2$; SO$_2$NHC$_{1-6}$alkyl(R$^q$)$_3$; SO$_2$N(C$_{1-6}$alkyl(R$^q$)$_3$)$_2$; NHSO$_2$C$_{1-6}$alkyl(R$^q$)$_3$; NHSO$_2$aryl(R$^q$)$_3$; NHSO$_2$heteroary(R$^q$)$_3$; —OC(O) heterocyclyl(R$^q$)$_3$; N(R$^{q'}$)C(O)C$_{1-6}$ alkyl(R$^q$)$_3$; NR$^{q'}$C (O)NH(C$_{1-6}$ alkyl(R$^q$)$_3$); —OC(O)C$_{1-6}$ alkyl(R$^q$)$_3$; —OC(O)aryl(R$^q$)$_3$; —OC(O)heteroaryl(R$^q$)$_3$; —C(=NR$^{q'}$)NH$_2$; —C(=N$^{q'}$)NHC$_{1-6}$ alkyl(R$^q$)$_3$; —C(=N$^{q'}$)N(C$_{1-6}$ alkyl(R$^q$)$_3$)$_2$;

—O—[C(O)—(CH$_2$)$_j$—CR$^5$R$^6$—(CH$_2$)$_k$—NR$^7$]$_p$R$^8$ and

—[NR$^7$(CH$_2$)$_k$—CR$^5$R$^6$—(CH$_2$)$_j$—C(O)]$_p$OR$^9$ wherein j and k independently represent integers of from 0–3;

R$^5$ and R$^6$ are independently H, aryl, C$_{1-6}$ alkyl(R$^q$)$_3$, or CR$^5$R$^6$ in combination represents a 3, 4, 5 or 6 membered cycloalkyl or heterocyclyl group, an aryl group or a heteroaryl group;

p represents 1, 2 or 3, with the proviso that when p represents 1, CR$^5$R$^6$ represents a 3, 4, 5 or 6 membered cycloalkyl group or a heterocyclyl group, an aryl group or a heteroaryl group, and at least one of j and k is 1, 2 or 3;

R$^7$ and R$^8$ are independently H, C$_{1-6}$ alkyl or aryl;

R$^9$ represents H, a negative charge balanced by a positively charged group or a protecting group;

R$^q$ represents a member selected from the group consisting of: R$^{q'}$; halo; CN; CO$_2$H; CO$_2$C$_{1-4}$ alkyl; C(O)C$_{1-4}$ alkyl; NH(R$^{q''}$); aryl(R$^q$)$_3$; heteroaryl(R$^q$)$_3$; NHC$_{1-4}$ alkyl; N(C$_{1-4}$ alkyl)$_2$; CONH$_2$; SH; S(O)$_y$C$_{1-6}$ alkyl(R$^q$) $_3$; C(O)NHC$_{1-6}$ alkyl(R$^q$)$_3$; C(O)N(C$_{1-6}$ alkyl(R$^q$)$_3$)$_2$; C$_{3-8}$ cycloalkyl; NHC(NH)NH$_2$; -heteroalkyl(R$^q$)$_3$; —NHC(O)NH$_2$;

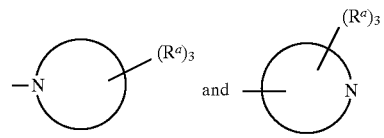

wherein

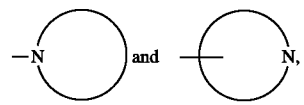

independently represent mono or bicyclic ring systems, non-aromatic or partially aromatic, containing from 5–10 ring atoms, 1–4 of which are N and 0–1 of which are O or S(O)$_y$, with y equal to 0, 1 or 2, optionally containing 1–2 carbonyl groups;

each R$^a$ independently represents a member selected from the group consisting of: H, C$_{1-6}$ alkyl, OC$_{1-6}$ alkyl, aralkyl, substituted aralkyl, heteroaralkyl, substituted heteroaralkyl, aralkoxy, substituted aralkoxy, halo, hydroxy, CN, CONH$_2$, CONHC$_{1-6}$ alkyl, CON(C$_{1-6}$ alkyl)$_2$, CO$_2$H, CO$_2$C$_{1-6}$ alkyl, C(O)C$_{1-6}$ alkyl, phenyl, CF$_3$, SH, NO$_2$, SO$_y$C$_{1-6}$ alkyl, with y as defined above; SO$_2$NH$_2$, SO$_2$NHC$_{1-6}$ alkyl, NHSO$_2$(substituted aryl), NHSO$_2$(substituted heteroaryl), NHSO$_2$C$_{1-6}$alkyl, NHSO$_2$aryl, NHSO$_2$heteroaryl, NH$_2$, NHC$_{1-6}$ alkyl, N(C$_{1-6}$ alkyl)$_2$, NHC(O)C$_{1-6}$ alkyl, NHC(O)NH(C$_{1-6}$ alkyl), C$_{2-4}$ alkenyl and C$_{2-4}$ alkynyl;

R$^{q'}$ represents H, OH, C$_{1-4}$ alkyl, —OC$_{1-4}$ alkyl, aryl or C(O)C$_{1-4}$ alkyl, and R$^{q''}$ represents H, OH or OC$_{1-4}$ alkyl.

2. A compound in accordance with claim 1 wherein one or two R" groups are present, and each independently represents NH$_2$, NHC$_{1-6}$ alkyl(R$^q$)$_3$, N(C$_{1-6}$ alkyl)$_2$, NHC$_{3-8}$ cycloalkyl, N(R$^{q'}$)C(O)C$_{1-6}$ alkyl(R$^q$)$_3$, C$_{1-6}$ alkyl(R$^q$)$_3$, OC$_{1-6}$ alkyl(R$^q$)$_3$, CO$_2$H, CONH$_2$, NR$^{q'}$C(O)NHC$_{1-6}$ alkyl (R$^q$)$^3$ or heterocyclyl(R$^q$)$_3$.

3. A compound in accordance with claim 1 wherein: HETCy represents a 5–6 membered non-aromatic heterocycle with 1–2 nitrogen atoms contained therein.

4. A compound in accordance with claim 3 wherein HETCy represents a pyrrolidinyl or piperidinyl group.

5. A compound in accordance with claim 4 wherein HETCy represents a 4-piperidinyl group.

6. A compound in accordance with claim 1 wherein R' is selected from C$_{1-6}$ alkyl(R$^q$)$_3$, OC$_{1-6}$ alkyl(R$^q$)$_3$, —C(O)C$_{1-6}$ alkyl(R$^q$)$_3$; CN, NO$_2$ and CO$_2$C$_{1-6}$ alkyl(R$^q$)$_3$.

7. A compound in accordance with claim 1 wherein from 1–3 R groups are present and each independently represents a member selected from the group consisting of: halo, hydroxy, C$_{1-6}$ alkyl(R$^q$)$_3$, OC$_{1-6}$ alkyl(R$^q$)$_3$, NH$_2$, NHC$_{1-6}$ alkyl(R$^q$)$_3$, N(C$_{1-6}$ alkyl(R$^q$)$_3$)$_2$ and CF$_3$.

8. A compound in accordance with claim 7 wherein one or two R groups are present, selected from halo and CF$_3$.

9. A compound in accordance with claim 1 wherein $R^x$ is H, $C_{3-8}$ cycloalkyl or $C_{1-6}$ alkyl$(R^q)_3$.

10. A compound in accordance with claim 9 wherein $R^x$ represents H, $CH_3$, $CH_2CH_3$, $CH_2CH_2CH_3$, $CH_2CH_2CH_2CH_3$,

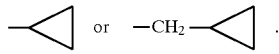

11. A compound in accordance with claim 1 wherein X' represents a direct bond.

12. A compound in accordance with claim 1 wherein X represents $-(CH_2)_m-Y-(CH_2)_n-$, Y represents a direct bond, O, S or C(O); m represents 0 or 1 and n represents 0 or 1.

13. A compound in accordance with claim 12 wherein X represents a direct bond.

14. A compound in accordance with claim 1 wherein one or two R" groups are present, each independently representing $NH_2$, $NHC_{1-6}$ alkyl$(R^q)_3$, $N(C_{1-6}$ alkyl$)_2$, $NHC_{3-8}$ cycloalkyl, $N(R^q)C(O)C_{1-6}$ alkyl$(R^q)_3$, $C_{1-6}$ alkyl$(R^q)_3$, $OC_{1-6}$alkyl$(R^q)_3$, $CO_2H$, $CONH_2$, $NR^qC(O)NHC_{1-6}$alkyl$(R^q)^3$ or heterocyclyl$(R^q)_3$;

HETCy represents a 5–6 membered non-aromatic heterocyclyl with 1–2 nitrogen atoms contained therein, R' is selected from $C_{1-6}$ alkyl$(R^q)_3$, $OC_{1-6}$ alkyl$(R^q)_3$, $-C(O)C_{1-6}$alkyl$(R^q)_3$; CN; $NO_2$; and $CO_2C_{1-6}$alkyl$(R^q)_3$;

from 1–3 R groups are present and each independently represents a member selected from the group consisting of: halo, hydroxy, $C_{1-6}$ alkyl$(R^q)_3$, $OC_{1-6}$ alkyl$(R^q)_3$, $NH_2$, $NHC_{1-6}$ alkyl$(R^q)_3$, $N(C_{1-6}$ alkyl$(R^q)_3)_2$ $CO_2H$ and $CF_3$;

$R^x$ is H, $C_{3-8}$ cycloalkyl or $C_{1-6}$ alkyl$(R^q)_3$;

X' represents a direct bond;

X represents $-(CH_2)_m-Y-(CH_2)_n-$, Y represents a direct bond; m represents 0 or 1 and n represents 0 or 1.

15. A compound in accordance with claim 14 wherein:

one or two R" groups are present, selected from the group consisting of: $NH_2$, $NHC_{1-6}$ alkyl$(R^q)_3$, $N(C_{1-6}$ alkyl$)_2$, $C_{1-6}$ alkyl$(R^q)_3$, $OC_{1-6}$ alkyl$(R^q)_3$ and heterocyclyl$(R^q)_3$;

HETCy represents a piperidinyl group;

zero or one R' is present, which is selected from $C_{1-6}$ alkyl$(R^q)_3$, $-CO_2C_{1-6}$ alkyl$(R^q)_3$ and $-C(O)C_{1-6}$ alkyl$(R^q)_3$;

one or two R groups are present, selected from halo and $CF_3$;

$R^x$ is H, $C_{3-8}$ cycloalkyl or $C_{1-6}$ alkyl$(R^q)_3$; and

X and X' represent a direct bond.

16. A compound in accordance with claim 14 wherein: one R" group is present and is selected from:

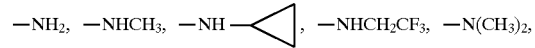

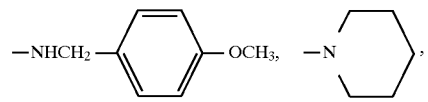

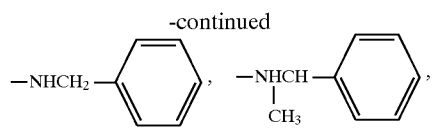

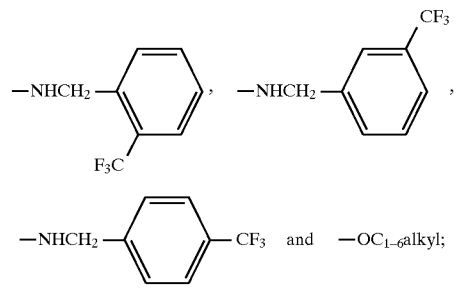

HETCy represents a 4-piperidinyl group;

R' is absent;

one or two R groups are present selected from halo and $CF_3$;

$R^x$ represents H, $CH_3$, $CH_2CH_3$, $CH_2CH_2CH_3$, $CH_2CH_2CH_2CH_3$,

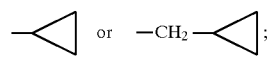

and X and X' represent direct bonds.

17. A pharmaceutical composition comprised of a compound in accordance with claim 1 in combination with a pharmaceutically acceptable carrier.

18. A method of treating a cytokine mediated disease in a mammalian patient in need of such treatment comprising administering to said mammal a compound in accordance with claim 1 in an amount which is effective to treat said cytokine mediated disease.

19. A method in accordance with claim 18 wherein the cytokine mediated disease is rheumatoid arthritis, osteoarthritis, endotoxemia, toxic shock syndrome, inflammatory bowel disease, tuberculosis, atherosclerosis, muscle degeneration, cachexia, psoriatic arthritis, Reiter's syndrome, rheumatoid arthritis, gout, traumatic arthritis, rubella arthritis or acute synovitis.

20. A method in accordance with claim 18 wherein the cytokine mediated disease is rheumatoid arthritis, rheumatoid spondylitis, osteoarthritis, gouty arthritis, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejection, fever, myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis or pyresis.

21. A compound represented by one of the structural formulas:

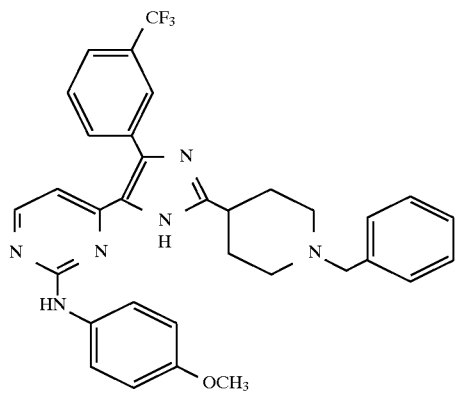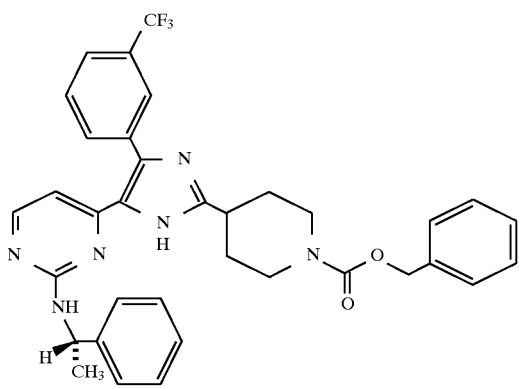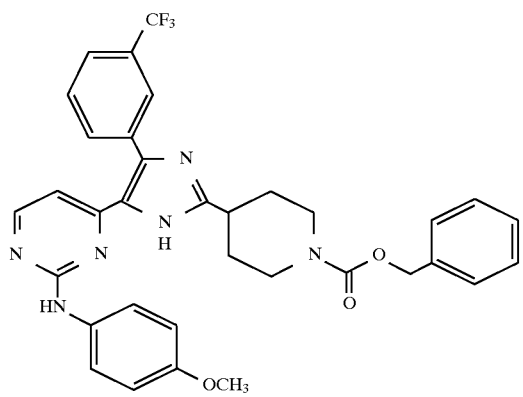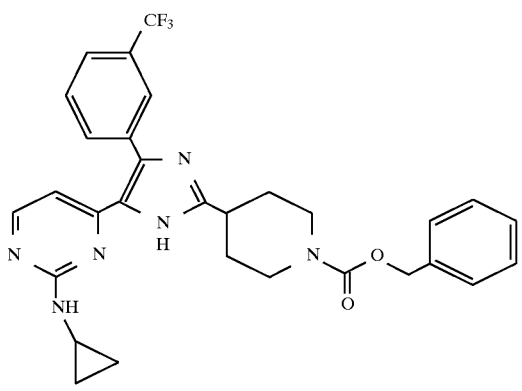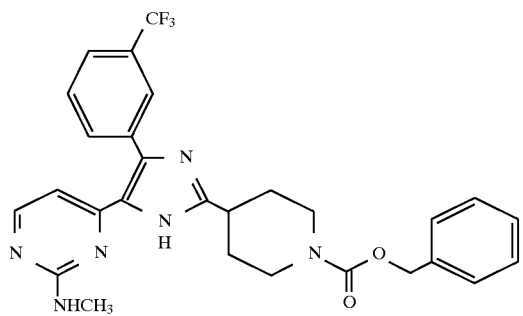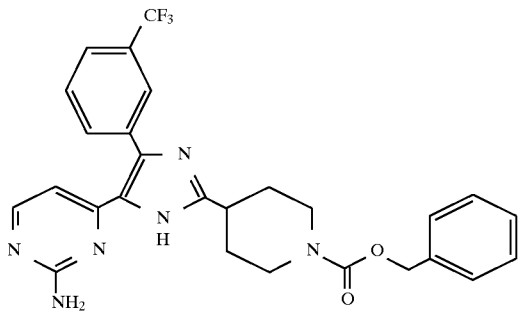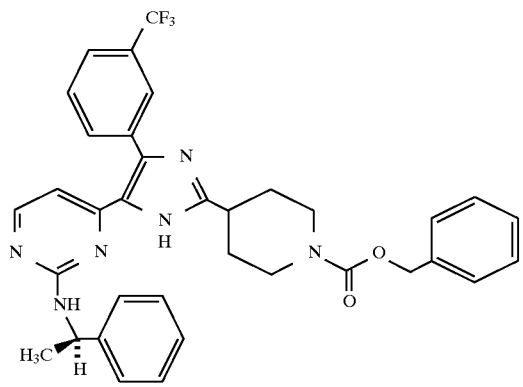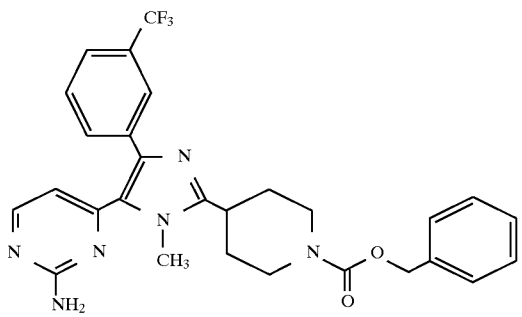

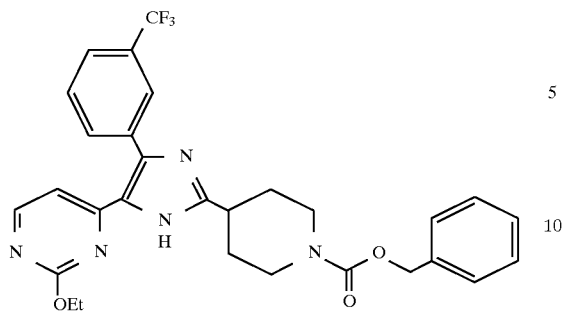
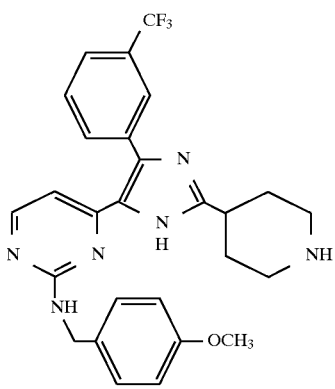
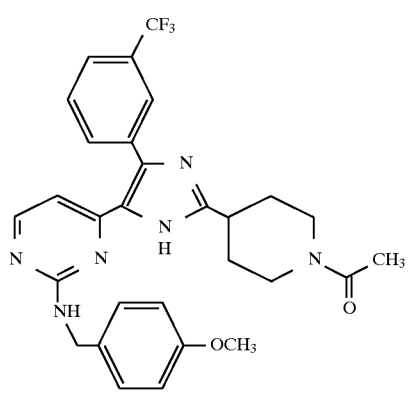
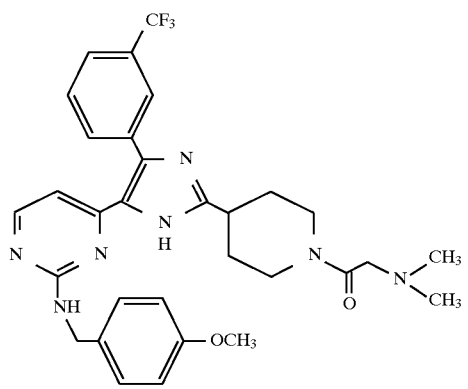

71
-continued
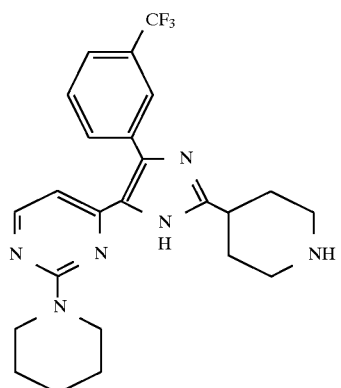
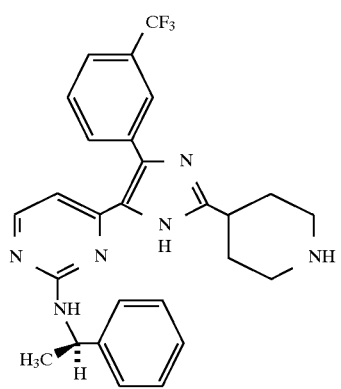
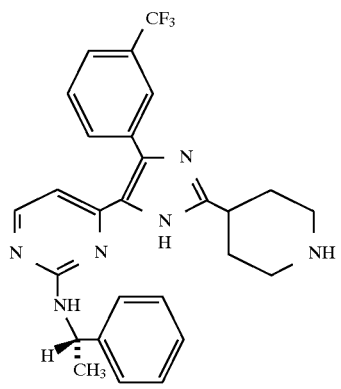
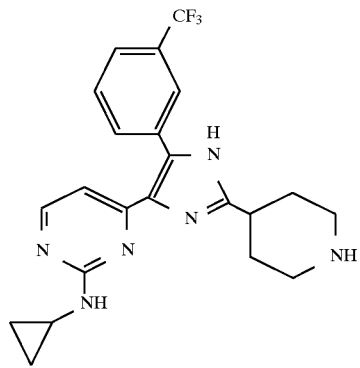
72
-continued
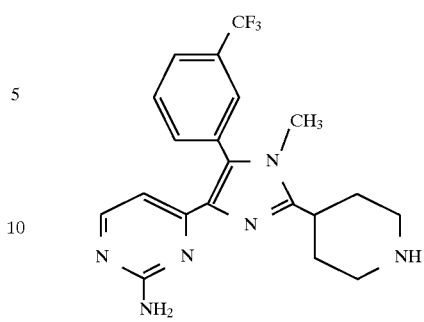
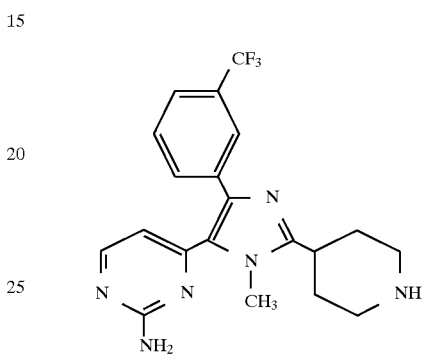
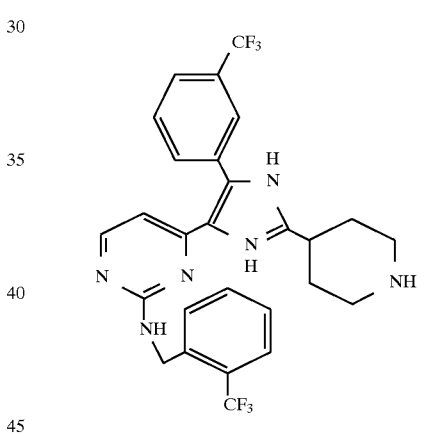
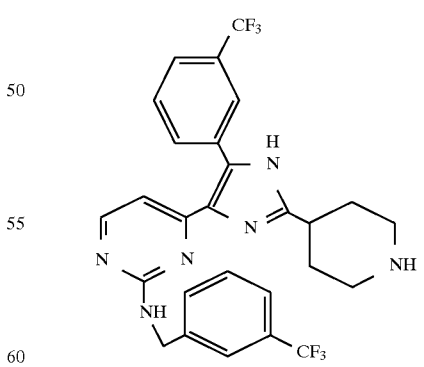

-continued
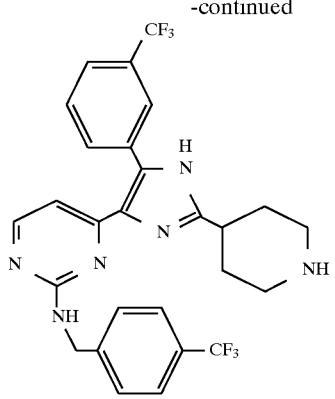
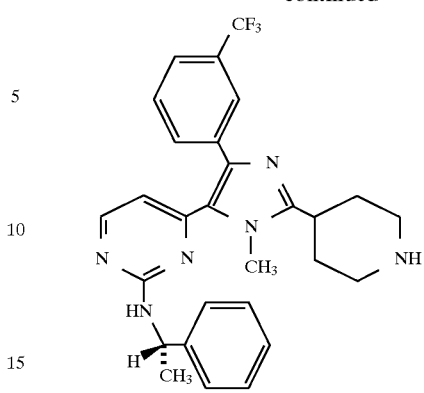
or a pharmaceutically acceptable salt thereof.
22. A compound represented by the formula:
or a pharmaceutically acceptable salt thereof.
23. A compound represented by the formula:
or a pharmaceutically acceptable salt thereof.

24. A compound represented by one of the structural formulas:
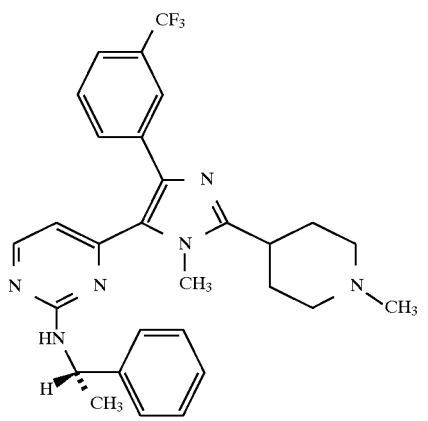
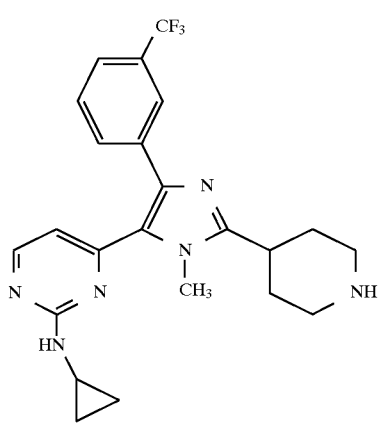
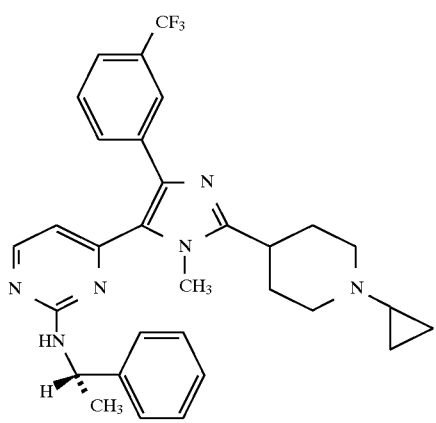
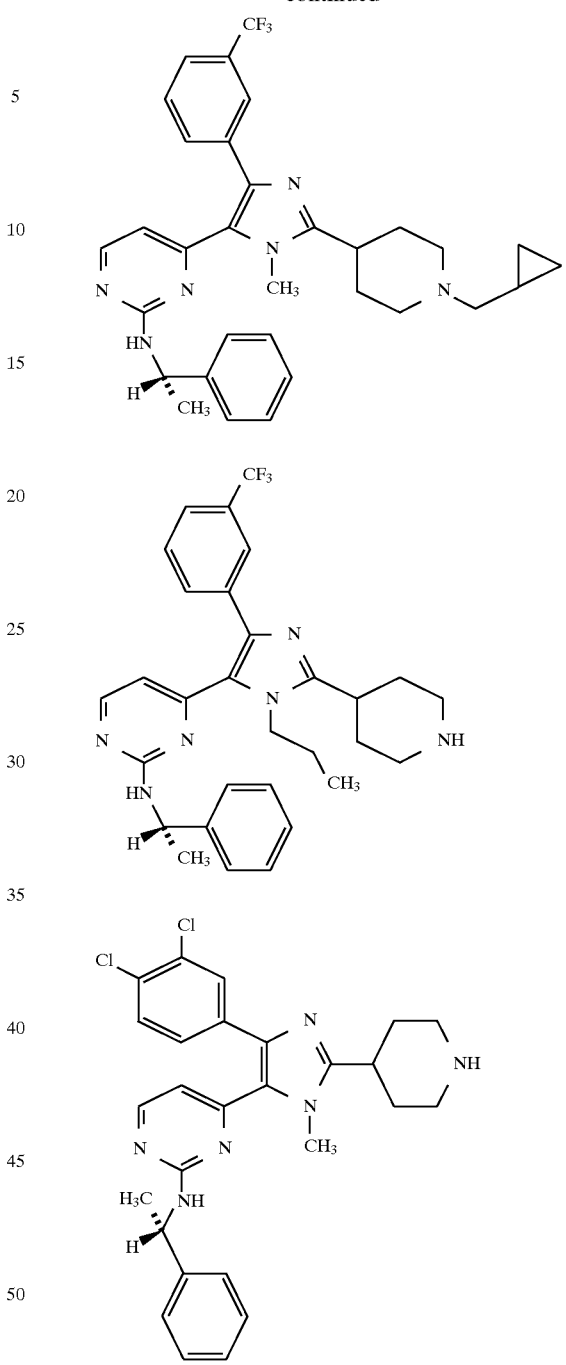

77
-continued
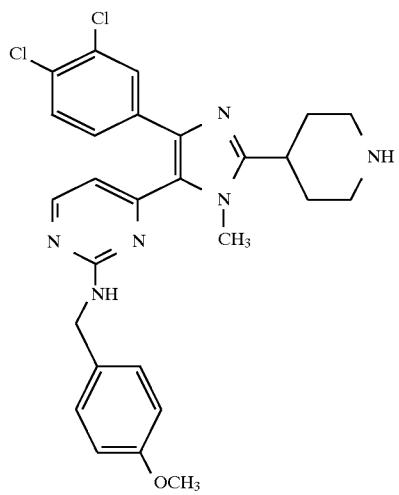
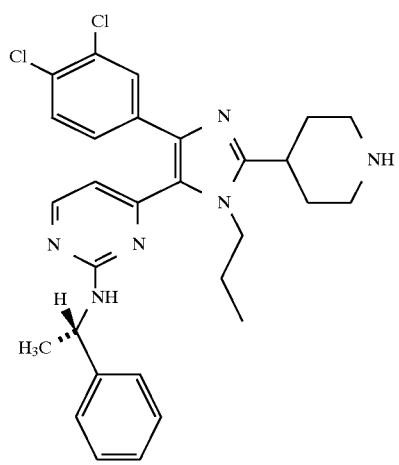
78
-continued
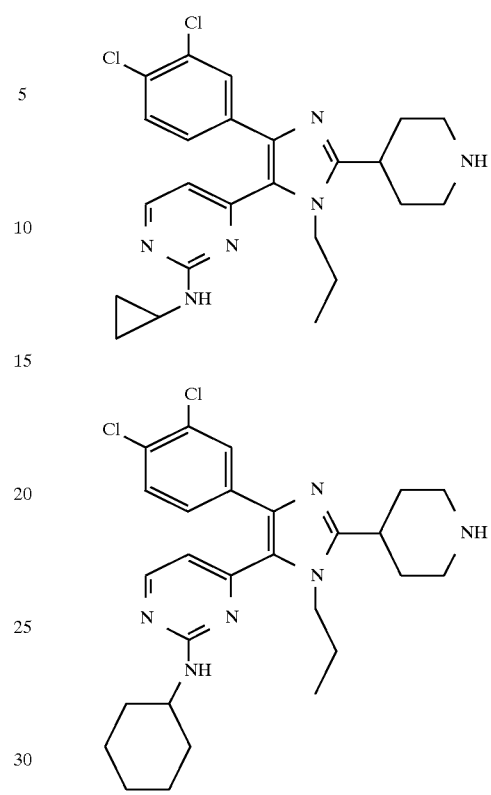
or a pharmaceutically acceptable salt thereof.
* * * * *